(12) United States Patent
Hara et al.

(10) Patent No.: US 7,852,551 B2
(45) Date of Patent: Dec. 14, 2010

(54) OPTICAL-SCANNING MICROSCOPE EXAMINATION APPARATUS

(75) Inventors: Mitsuhiro Hara, Musashino (JP); Hiroshi Tosaka, Hachioji (JP); Akihiro Horii, Brookline, MA (US); Kazunari Tokuda, Hachioji (JP); Yoshihisa Tanikawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 696 days.

(21) Appl. No.: 11/628,762

(22) PCT Filed: Jun. 9, 2005

(86) PCT No.: PCT/JP2005/010596

§ 371 (c)(1),
(2), (4) Date: Oct. 24, 2007

(87) PCT Pub. No.: WO2005/121862

PCT Pub. Date: Dec. 22, 2005

(65) Prior Publication Data

US 2008/0130103 A1     Jun. 5, 2008

(30) Foreign Application Priority Data

Jun. 14, 2004  (JP)  .............................. 2004-175520
Jul. 22, 2004  (JP)  .............................. 2004-214573

(51) Int. Cl.
*G02B 21/00* (2006.01)
(52) U.S. Cl. ...................................... 359/368; 359/385
(58) Field of Classification Search ................. 359/368, 359/379, 380, 384, 385, 389
See application file for complete search history.

(56) References Cited

U.S. PATENT DOCUMENTS 6,028,306 A * 2/2000 Hayashi ...................... 250/235

(Continued)

FOREIGN PATENT DOCUMENTS

JP     03-087804     4/1991

(Continued)

OTHER PUBLICATIONS

European Search Report dated Apr. 27, 2010.

*Primary Examiner*—Frank G Font
(74) *Attorney, Agent, or Firm*—Pillsbury Winthrop Shaw Pittman, LLP

(57) ABSTRACT

A clear image having suppressed blurring due to pulsing is obtained by in-vivo examination of biological tissue or various internal organs of mammals, including small laboratory animals. The invention provides an optical-scanning microscope examination apparatus including a light source; a light-transmitting member for transmitting light from the light source; a collimator optical system for converting the transmitted light to a collimated beam; a beam-scanning unit for scanning the collimated beam on a subject; a focusing optical system for focusing the scanned beam onto the subject; a pupil-projection optical system; a light detector for detecting return light returning from the subject via the focusing optical system, the pupil-projection optical system, the beam-scanning unit, the collimator optical system, and the light-transmitting member; an actuator for moving the collimator optical system in an optical-axis direction; a control apparatus for controlling driving thereof; and a deflecting mechanism for deflecting the light issuing from the light-transmitting member in a direction intersecting the optical axis thereof, wherein the actuator is disposed in a space parallel to a plane including optical axes before and after deflection by the deflecting mechanism.

28 Claims, 16 Drawing Sheets

U.S. PATENT DOCUMENTS

| | | | |
|---|---|---|---|
| 6,128,127 A * | 10/2000 | Kusaka | 359/371 |
| 6,697,196 B2 * | 2/2004 | Suzuki | 359/385 |
| 6,831,781 B2 * | 12/2004 | Tearney et al. | 359/385 |
| 6,963,398 B2 * | 11/2005 | Sasaki et al. | 356/318 |
| 7,167,305 B2 * | 1/2007 | Ogihara | 359/382 |
| 2002/0043622 A1 | 4/2002 | Birk et al. | 250/306 |
| 2002/0176683 A1 | 11/2002 | Harman et al. | 385/137 |
| 2004/0080817 A1 * | 4/2004 | Yamaguchi | 359/385 |
| 2004/0114224 A1 | 6/2004 | Rigler et al. | 359/383 |

FOREIGN PATENT DOCUMENTS

| | | |
|---|---|---|
| JP | 05-072481 | 3/1993 |
| JP | 5-119130 | 5/1993 |
| JP | 2001-356256 | 12/2001 |
| JP | 2003-043374 | 2/2003 |
| JP | 2003-172878 | 6/2003 |
| JP | 2003-207718 | 7/2003 |
| JP | 2003-307682 | 10/2003 |
| JP | 2003-344777 | 12/2003 |
| WO | WO 02/077694 | 10/2002 |

* cited by examiner

OPTICAL-SCANNING MICROSCOPE EXAMINATION APPARATUS

This is the U.S. National Stage of International Application No. PCT/JP2005/010596, filed on Jun. 9, 2005, which, in turn, relies for priority upon Japanese Patent Application No. 2004-175520, filed on Jun. 14, 2004, and Japanese Patent Application No. 2004-214573, filed on Jul. 22, 2004, the contents of all of which are incorporated herein by reference in their entireties.

TECHNICAL FIELD

The present invention relates to an optical-scanning microscope examination apparatus.

BACKGROUND ART

As optical-scanning microscope examination apparatuses in the related art for performing magnified observation of a subject, there are those having the structures disclosed in Patent Document 1 and Patent Document 2. In these optical-scanning microscope examination apparatuses disclosed in Patent Documents 1 and 2, a lens driving mechanism is provided in an objective lens for rapidly aligning the focal position relative to the subject with an examination site.

In addition, a laser-scanning confocal microscope is a known apparatus for examining cellular function and so on by illuminating a specimen such as a living organism with excitation light from the surface thereof and selectively detecting fluorescence produced from a predetermined depth position in the specimen (for example, see Patent Documents 3 and 4).

This laser-scanning confocal fluorescence microscope, in addition to general microscope observation, scans a laser beam, which is focused to a minute spot region, using a scanning mechanism such as a galvanometer mirror or the like an detects the fluorescence emitted from the specimen to acquire an image.

Because this laser-scanning confocal microscope has excellent resolving power and can eliminate light outside of the minute spot being observed, it has the advantage that it is possible to acquire clear observation images with a high S/N ratio.

Patent Document 1: Japanese Unexamined Patent Application, Publication No. 2003-172878 ([0042], FIG. 2, etc.).

Patent Document 2: Japanese Unexamined Patent Application, Publication No. 2001-356256 ([0020], FIG. 2, etc.).

Patent Document 3: Japanese Unexamined Patent Application, Publication No. Hei 3-87804 (page 2, etc.).

Patent Document 4: Japanese Unexamined Patent Application, Publication No. Hei 5-72481 (FIG. 1, etc.).

DISCLOSURE OF INVENTION

However, the optical-scanning microscope examination apparatuses of the related art perform examination by positioning the objective lens at a predetermined distance relative to the subject, and are not assumed to perform examination of various internal organs of a small laboratory animal, such as a rat or mouse, while still alive (in vivo). In other words, when performing in-vivo examination of a subject such as a small laboratory animal, in order to prevent image blurring due to a pulse thereof, it is effective to perform examination with the tip of the objective lens pressed against the subject; however, in order to focus at the examination site using the lens driving mechanism provided in the objective lens, the optical-scanning microscope examination apparatuses of the related art have a construction in which the end surface of the objective lens is moved. Thus, the optical-scanning microscope examination apparatuses of the related art cannot perform examination with the end surface of the objective lens in contact with the living organism, and unless another method is used, they suffer from the drawback that the image is blurred due to the pulsing, and it is not possible to acquire a clear image.

Furthermore, when carrying out magnified observation of the condition of internal tissue of a small laboratory animal or the like, there are also instances in which it is necessary to also observe the external condition of the small laboratory animal in parallel; in such a case, it is conceivable to carry out observation by combining the optical-scanning microscope examination apparatus with a stereomicroscope apparatus which can observe a wide area at a lower magnification. Therefore, the optical-scanning microscope examination apparatus must have a construction which does not block, as far as possible, the field of view of the stereomicroscope apparatus.

In addition, when examining these various internal organs of a small laboratory animal using a microscope, including the laser-scanning confocal microscopes of the related art, it is necessary to cut open the skin or muscle tissue or to bore a hole in the cranial bone to expose the internal organs. However, because the size of the objective lens disposed close to the examination site is large compared to the small laboratory animal, when examining the internal organs, it is necessary to make a large incision in the skin, muscle tissue or the like, or to form a large hole.

In this case, although examination is possible directly after making the incision in the tissue or directly after boring the hole, because substantial damage is done to the small laboratory animal, it is difficult to perform time-lapse observation for an extended period of time. A method in which the incision is sutured directly after observation and an incision is made again at the next observation is conceivable; however, considering the damage done to the small laboratory animal, there is the drawback that it is difficult to perform observation under normal conditions as time passes.

The present invention has been conceived in light of the circumstances described above, and an object thereof is to provide an optical-scanning microscope examination apparatus that can perform long-term in-vivo examination of biological tissue, such as cells and muscles, or various internal organs, such as the heart and liver, of mammals, including small laboratory animals; that can acquire clear images in which blurring due to a pulse is reduced; and that can be reduced in size so that, as far as possible, it does not block the field of view of a stereomicroscope apparatus.

In order to realize the object described above, the present invention provides the following solutions.

The invention provides an optical-scanning microscope examination apparatus comprising a light source; a light-transmitting member for transmitting light from the light source; a collimator optical system for converting the light transmitted by the light-transmitting member into a collimated beam; a beam scanning unit for scanning the collimated beam issuing from the collimator optical system on a subject; a focusing optical system for focusing the beam scanned by the beam-scanning unit on the subject; a pupil-projection optical system which is disposed between the focusing optical system and the beam-scanning unit; a light detector for detecting return light returning from the subject via the focusing optical system, the pupil-projection optical system, the beam-scanning unit, the collimator optical system, and the light-transmitting member; an actuator for moving an end portion of the light-transmitting member, the collimator optical system, or the pupil-projection optical system in an optical-axis direction; a control apparatus for controlling driving of the actuator; and a deflecting mechanism for deflecting the light issuing from the light-transmitting member in a direction intersecting the optical axis thereof, wherein the actuator is disposed in a space parallel to a plane including optical axes before and after deflection by the deflecting mechanism.

According to the present invention, the light emitted from the light source is transmitted through the light-transmitting member and is converted to a collimated beam by the collimator optical system. The collimated beam from the collimator optical system is scanned by the beam-scanning unit and is radiated through the pupil-projection optical system and the focusing optical system onto the subject. Return light from the subject returns along the same path via the focusing optical system, the pupil-projection optical system, the beam-scanning unit, the collimator optical system, and the light-transmitting member and is detected by the light detector.

The light issuing from the light-transmitting member is deflected in an intersecting direction by the deflecting mechanism. Therefore, it is possible to guide the light towards the subject from a lateral direction relative to the optical-axis direction of the focusing optical system. As a result, the height dimension, from the subject, of the optical system from the collimator optical system to the focusing optical system can be reduced, thus making it possible to ensure that it does not interfere with the stereomicroscope disposed thereabove.

Because the actuator which moves any one of the end portion of the light-transmitting member, the collimator optical system, and the pupil-projection optical system is disposed in a space parallel to the plane including the optical axes before and after deflection by the deflecting mechanism, the actuator does not protrude in the lateral direction, and therefore, it is possible to reduce the projection area on the subject so that it does not interfere with the stereomicroscope.

By operating the control apparatus to actuate the actuator to move any one of the end portion of the light-transmitting member, the collimator optical system, and the pupil-projection optical system in the optical-axis direction, it is possible to change the focal position while keeping the tip of the focusing optical system fixed in position. In other words, it is possible to perform examination with the tip of the focusing optical system pressed against the subject, such as a small laboratory animal. As a result, it is possible to prevent image blurring due to the pulse of the subject, and clear images can thus be acquired.

In the optical-scanning microscope examination apparatus according to the present invention, a connecting portion for the actuator and the end portion of the light-transmitting member, the collimator optical system, or the pupil-projection optical system may be connected in such a manner as to be capable of rotating about an axis orthogonal to the plane including the optical axes before and after deflection by the deflecting mechanism.

According to this optical-scanning microscope examination apparatus, when the end portion of the light-transmitting member, the collimator optical system, or the pupil projection optical system is moved by operating the actuator, a force is applied to the connecting portion from the actuator. When the end portion of the light-transmitting member, the collimator optical system, or the pupil-projection optical system is reduced in size, a wrenching force acts due to friction with the surroundings when displacement occurs; however, by rotating the connecting portion about an axis orthogonal to the optical axes before and after deflection by the deflecting mechanism to lessen this force, it is possible to achieve smooth motion.

In the optical-scanning microscope examination apparatus according to the present invention, the deflecting mechanism may be constituted by the beam scanning unit.

By making the beam scanning unit also serve as the deflecting mechanism, it is possible to decrease the number of parts and to reduce the size of the apparatus.

The optical-scanning microscope examination apparatus according to the present invention may further comprise a position detector for detecting the position of the end portion of the light-transmitting member, the collimator optical system, or the pupil-projection optical system.

Detecting the position of the end portion of the light-transmitting member, the collimator optical system, or the pupil-projection optical system with the position detector allows more precise control.

In the optical-scanning microscope examination apparatus according to the present invention, the collimator optical system may be provided so as to be capable of moving and may include a transparent member forming a seal between an end surface of the light-transmitting member and the collimator optical system.

It is conceivable that dust is produced from sliding parts and the like due to movement of the collimator optical system; however, due to the function of the transparent member, it is possible to prevent the dust produced from adhering to the end surface of the light-transmitting member.

In the optical-scanning microscope examination apparatus according to the present invention, the light source may be capable of emitting light of a plurality of wavelengths and may include a selecting mechanism for selecting the wavelength of the light emitted from the light source, and the control apparatus may control the actuator according to the wavelength selected by the selecting mechanism.

When switching the wavelength of the light source, the focal position changes according to the wavelength, and therefore, by controlling the actuator according to the wavelength with the control apparatus, it is possible to reduce the incidence of chromatic aberrations, and the number of lenses can be reduced.

In the optical-scanning microscope examination apparatus according to the present invention, the end portion of the light-transmitting member, the collimator optical system, the beam-scanning unit, and the pupil-projection optical system may be accommodated inside a chassis.

Furthermore, in the optical-scanning microscope examination apparatus according to the present invention, a window through which it is possible to observe part of the end portion of the light-transmitting member, the collimator optical system, or the pupil-projection optical system from outside may be provided in the chassis.

By doing so, the user can easily confirm the current magnification from the position of part of the end portion of the light-transmitting member, the collimator optical system or the pupil-projection optical system that can be seen through the window.

In the optical-scanning microscope examination apparatus according to the present invention, the focusing optical system may be attached to the chassis in such a manner as to be capable of being attached and removed.

By allowing the optical system to be attached to and removed from the chassis, it is possible to keep the focusing optical system set at the subject. Therefore, it is possible to fix the focusing optical system relative to the subject, which allows long-term observation of the same position on the subject.

In the optical-scanning microscope examination apparatus according to the present invention, a code indicating information inherent to the focusing optical system may be provided in the focusing optical system, a reading apparatus for reading the code may be provided in the chassis, and the control apparatus may control the actuator based on the read code.

Because there are individual differences in focusing optical systems, when changing one focusing optical system to another focusing optical system, the control apparatus can perform the correct focal position adjustment for each focusing optical system using the actuator by reading the code with the reading apparatus.

In the optical-scanning microscope examination apparatus according to the present invention, the chassis may be connected by a connector in such a manner as to be capable of being attached to and removed from the control apparatus; an in-chassis-optical-system code indicating information inherent to the collimator optical system and the pupil-projection optical system may be provided on the chassis; an in-chassis-optical-system information reading apparatus for reading the in-chassis-optical-system code may be provided in the connector; and the control apparatus may control the actuator based on the read in-chassis-optical-system code.

When the chassis and the control apparatus are connected with the connector, the in-chassis-optical-system code provided on the chassis is read by the in-chassis-optical-system information reading apparatus provided in the connector. Because there is an optical system having inherent information in the chassis, such as the collimator optical system and the pupil-projection optical system, by reading it and controlling the actuator based on the read in-chassis optical system code, it is possible to perform focal position adjustment with better precision.

An optical-scanning microscope examination apparatus according to the present invention is an optical-scanning microscope examination apparatus comprising a light source; a light-transmitting member for transmitting light from the light source; a collimator optical system for converting the light transmitted by the light-transmitting member to a collimated beam; a beam-scanning unit for scanning the collimated beam issuing from the collimator optical system on a subject; a focusing optical system for focusing the beam scanned by the beam-scanning unit on the subject; a pupil-projection optical system disposed between the focusing optical system and the beam scanning unit; a light detector for detecting return light returning from the subject via the focusing optical system, the pupil-projection optical system, the beam-scanning unit, the collimator optical system, and the light-transmitting member; an actuator for moving the end portion of the light-transmitting member, the collimator optical system, or the pupil-projection optical system in the optical-axis direction; and a control apparatus for controlling driving of the actuator, wherein an end portion of the light-transmitting member, the collimator optical system, the beam scanning unit, and the pupil-projection optical system are accommodated inside a chassis, and the focusing optical system is attached to the chassis in such a manner as to be capable of being attached and removed.

According to the present invention, by operating the control apparatus to actuate the actuator and move any one of the end portion of the light-transmitting member, the collimator optical system, and the pupil-projection optical system in the optical-axis direction, it is possible to change the focal position while keeping the position of the end of the focusing optical system fixed. In other words, it is possible to perform examination with the end of the focusing optical system pressed against the subject, such as a small laboratory animal. As a result, it is possible to prevent image blurring due to the pulse of the subject, and clear images can thus be acquired.

In this case, by making it possible to attach and remove the focusing optical system to and from the chassis, it is possible to keep the focusing optical system set at the subject. Therefore, it is possible to perform observation of the same position of the subject over an extended period of time with the focusing optical system fixed with respect to the subject.

In the optical-scanning microscope examination apparatus according to the present invention, a code indicating information inherent to the focusing optical system may be provided in the focusing optical system; a reading apparatus for reading the code may provided in the chassis; and the control apparatus may control the actuator based on the read code.

According to such an optical-scanning microscope examination apparatus, even if there are errors inherent to each focusing optical system, they can be corrected when mounting the focusing optical system, and predetermined image settings or image information during acquisition can be displayed.

The optical-scanning microscope examination apparatus according to the present invention may further comprise a database for associating and storing the code and the information inherent to the focusing optical system, wherein the control apparatus searches the database using as a key the code read by the reading apparatus and controls the actuator based on the obtained information inherent to the focusing optical system.

By doing so, it is possible to store information inherent to the focusing optical system in the database and to thus simplify the code. In addition, it is possible to acquire many types of information, such as lens data and aberrations, using the simple code, which allows more precise control of the actuator to be performed.

In the optical-scanning microscope examination apparatus according to the present invention, the chassis may be connected via a connector in such a manner as to be capable of being attached to and removed from the control apparatus; an in-chassis-optical-system code indicating information inherent to the collimator optical system and the pupil-projection optical system may be provided in the chassis; an in-chassis-optical-system information reading apparatus for reading the in-chassis-optical-system code may be provided in the connector; and the control apparatus may control the actuator based on the read in-chassis-optical-system code.

When the chassis and the control apparatus are connected with the connector, the in-chassis-optical-system code provided on the chassis is read by the in-chassis-optical-system information reading apparatus provided in the connector. Because there is an optical system having inherent information in the chassis, such as the collimator optical system or the pupil-projection optical system, by reading it and controlling the actuator based on the read in-chassis-optical-system code, it is possible to perform more precise focal position adjustment.

The optical-scanning microscope examination apparatus according to the present invention may further comprise a second database for associating and storing the in-chassis-optical-system code and information inherent to the collimator optical system and the pupil-projection optical system, wherein the control apparatus searches the second database using as a key the in-chassis-optical-system code read by the in-chassis-optical-system information reading apparatus and controls the actuator based on the obtained information.

By doing so, it is possible to simplify the in-chassis-optical-system code. In addition, using the simple code, it is possible to obtain many types of information, such as lens data and aberrations, from the second database, and it is possible to perform more precise control of the actuator.

The optical-scanning microscope examination apparatus according to the present invention may further comprise an image-information inputting unit for inputting image information of the image to be acquired by the light detector, wherein the control apparatus controls the actuator based on the image information.

When the operator inputs image information about the image to be acquired using the image-information inputting unit, the actuator is controlled by the control unit based on the input image information. Because the actuator is controlled automatically, it is possible to eliminate the adjustment procedure.

In the optical-scanning microscope examination apparatus according to the present invention, the image-information inputting unit may be provided on an outer face of the chassis.

With the user inputting image information on the outer surface of the chassis, the actuator is controlled based on the input image information. By providing an image-information inputting unit on the outer surface of the chassis, the ease of use can be improved.

The optical-scanning microscope examination apparatus according to the present invention may further comprise a position detector for detecting the position of the end portion of the light-transmitting member, the collimator optical system, or the pupil-projection optical system, which are moved by the actuator.

By detecting the position of the end portion of the light-transmitting member, the collimator optical system, or the pupil-projection optical system using the position detector, it is possible to achieve more precise control.

The optical-scanning microscope examination apparatus according to the present invention may further comprise an image-information calculating unit for calculating the image information of the image to be acquired by the light detector based on the position of the end portion of the light-transmitting member, the collimator optical system, or the pupil-projection optical system detected by the position detecting unit, and an image-information display unit for displaying the calculated image information.

When the actuator is actuated, by operating the position detecting unit, the position of the end portion of the light-transmitting member, the collimator optical system, or the pupil-projection optical system is detected, and the image-information calculating unit calculates image information about the image to be acquired based on the detected position. Then, because the calculated image information is displayed on the image-information display unit, it is possible for the operator to determine the image information for the currently acquired image by looking at the display of the image-information display unit.

The optical-scanning microscope examination apparatus according to the present invention may further comprise an inherent-information inputting unit for inputting inherent information of the focusing optical system; an image-information calculating unit for calculating the image information for the image to be acquired by the light detector based on the position of the end portion of the light-transmitting member, the collimator optical system, or the pupil-projection optical system detected by the position detecting unit and the input information inherent to the focusing optical system; and an image-information display unit for displaying the calculated image information.

By doing so, because the image-information calculating unit calculates the image-information of the image to be acquired based on the position of the end portion of the light-transmitting member, the collimator optical system, or the pupil-projection optical system and the information inherent to the focusing optical system, higher-precision image information is displayed on the image-information display unit.

The optical-scanning microscope examination apparatus according to the present invention may further comprise an optical-system-information inputting unit for inputting information inherent to the collimator optical system and the pupil-projection optical system; an image-information calculating unit for calculating the image information of the image to be acquired by the light detector based on the position of the end portion of the light-transmitting member, the collimator optical system, or the pupil-projection optical system detected by the position detecting unit and the input information inherent to the collimator optical system and the pupil-projection optical system; and an image-information display unit for displaying the calculated image information.

Because the image-information calculating unit calculates the image information of the image to be acquired by the light detector unit using the information inherent to the collimator optical system and the pupil-projection optical system input via the optical-system-information inputting unit, it is possible to display higher precision image information regardless of individual differences in the collimator optical systems and the pupil-projection optical systems.

The optical-scanning microscope examination apparatus according to the present invention may relate to a storage container for accommodating a focusing optical system of a laser-scanning microscope that includes a beam scanning unit including an optical fiber, a collimator mechanism, and a beam scanning mechanism; and a focusing optical system which has a long, thin, rigid, cylindrical inserting portion and which is attached to the beam scanning unit in such a manner as to be capable of being attached and removed, wherein a code for indicating information inherent to the focusing optical system may be provided.

According to the present invention, it is possible to use a code for the focusing optical system even in cases where it is not possible to attach a code because the focusing optical system is too small. In addition, it is possible to input the code even when the focusing optical system is already attached to the living organism.

In the optical-scanning microscope examination apparatus according to the present invention, a guard mechanism that is capable of accommodating only the focusing optical system corresponding to the code may be provided.

With such a configuration, it is possible to establish a one-to-one correspondence between focusing optical systems and storage containers.

The present invention provides an optical-scanning microscope examination apparatus comprising a light source; an optical fiber for transmitting light from the light source; an apparatus main body accommodating a collimator optical system which converts the light transmitted by the optical fiber into a collimated beam and a beam-scanning mechanism for two-dimensionally scanning the collimated beam emitted from the collimator optical system; an objective unit which is attached to the apparatus main body in such a manner as to be capable of being attached and removed and which focuses the beam scanned by the beam-scanning mechanism at an examination site of a subject; and a light detector for detecting return light returning via the objective unit, the apparatus main body, and the optical fiber, wherein the objective unit has an end portion that is capable of being inserted inside the subject, and a mechanism for attaching and detaching the objective unit to the main body includes a rotation stop for stopping relative rotation of the objective unit, about a longitudinal axis, with respect to the apparatus main body during attachment and detachment.

According to the present invention, when the light emitted from the light source is transmitted through the optical fiber and is introduced into the apparatus main body, it is converted to a collimated beam by the collimator optical system disposed inside the apparatus main body, is continuously two-dimensionally scanned by the beam-scanning mechanism, and is focused at the examination site by the objective unit. Because the objective unit has an end portion which can be inserted into the living organism, the end portion is inserted into an incision provided in the living organism or a body cavity, and the two-dimensionally scanned beam irradiates the examination site located inside the living organism. Return light from the examination site returns via the objective unit, the apparatus main body, and the optical fiber and is detected by the light detector.

In this case, in the optical-scanning microscope examination apparatus according to the present invention, because the objective unit is attached in such a manner as to be capable of being attached to and removed from the apparatus main body, by separating the apparatus main body and the objective unit by operating the attaching-and-detaching mechanism, it is possible to keep the objective unit inserted in the living organism. Accordingly, when carrying out multiple examinations of the same examination site of the living organism over time, it is possible to perform examinations without shifting the objective unit relative to the examination site.

Because it is not necessary to shift the objective unit relative to the examination site, it is possible to continue observation of the same location, and because only the objective unit is left inserted in the living organism, the burden placed on the living organism is reduced, and it is possible to maintain stable observation conditions.

According to the present invention, because the attaching-and-detaching mechanism includes the rotation stop for stopping relative rotation of the objective unit with respect to the apparatus main body about the longitudinal axis when attaching and detaching it, relative rotation of the objective unit and the apparatus main body during attachment and detachment is prevented by the operation of the rotation stop. As a result, when separating the apparatus main body, with the end portion of the objective unit inserted in the living organism, it is possible to remove the apparatus main body without causing relative motion of the end portion of the objective unit with respect to the living organism. Similarly, also when attaching the apparatus main body to the objective unit remaining inserted in the living organism, it is possible to attach the apparatus main body without causing relative motion of the objective unit with respect to the living organism.

In the invention described above, the attaching-and-detaching mechanism may include a first screw which is held on one of the apparatus main body and the objective unit in such a manner as to be freely rotatable about the longitudinal axis, and a second screw which is provided on the other one of the apparatus main body and the objective unit and which is fastened on the first screw.

By rotating the first screw about the longitudinal axis with the objective unit inserted in the longitudinal-axis direction relative to the apparatus main body and with the first screw and the second screw engaged, the first screw and the second screw are fastened. At this time, because relative rotation of the objective unit and the apparatus main body is stopped by the rotation stop, they both approach each other in the longitudinal-axis direction as the first screw rotates. Because the first screw is held on one of the apparatus main body and the objective unit in such a manner as to be freely rotatable, it is possible to attach and detach the objective unit and the apparatus main body without relative rotation, using a simple configuration.

In the invention described above, preferably a pupil-projection optical system for forming an intermediate image of the beam scanned by the beam scanning mechanism is provided in the apparatus main body; abutting surfaces that abut when the apparatus main body and the objective unit are coupled together are provided; and the position of the abutting surfaces in the optical-axis direction is disposed at a position substantially coincident with the position of the intermediate image in the optical-axis direction.

With such a configuration, it is possible to reduce the effect of errors in position, orientation, and so forth when the objective unit is coupled to the apparatus main body.

In the invention described above, marks which are aligned when the objective unit is attached to the apparatus main body may be provided on the apparatus main body and the objective unit. It is possible to easily recognize the phase of the apparatus main body relative to the objective unit with the aid of the marks. Therefore, it is possible to easily align the phase of the apparatus main body with respect to an objective unit which is kept in the living organism, and it is thus possible to easily realize a state in which observation is possible.

In the invention described above, an insertion-depth detecting member for detecting the insertion depth of the objective lens unit is preferably provided on the outer circumference of the objective unit.

In other words, as the insertion-depth detecting member on the outer circumferential surface of the objective unit, it is preferable to provide marks, for example, the marks shown in FIG. 18A to FIG. 18C.

Regarding the marks shown in FIG. 18A, a plurality of lines separated by equal intervals in the longitudinal direction are disposed on the outer circumferential surface of the objective unit, along the circumferential direction. By setting the interval of these marks to a predetermined value, it is possible to determine the insertion depth of the objective unit in the subject by counting the number of marks exposed outside the subject A.

The marks shown in FIG. 18B are alternating regions between the lines; it is possible to recognize the insertion depth in a similar way as described above.

The marks shown in FIG. 18C are regions between the lines whose color density varies sequentially; for example, by processing the image of the stereomicroscope apparatus, it is possible to determine the insertion depth from the color density of the exposed portion.

In the invention describe above, anti-reflection treatment is preferably applied to the outer circumference of the objective unit.

In other words, as shown in FIG. 19 for example, in addition to the marks described above, it is preferable to apply anti-reflection treatment to the end portion of the objective unit.

By doing so, during observation with another examination apparatus, such as the stereomicroscope apparatus, it is possible to prevent light reflected by the outer surface of the objective unit from interfering with the observation. The anti-reflection treatment may include black coating, matte processing, reflection-reduction coating, and so forth.

According to the present invention, because it is possible to adjust the focal position without moving a light-radiating end face of the focusing optical system, it is possible to perform observation while adjusting the focal position, with the light-radiating end face of the focusing optical system pressed against the subject. In such a case, by disposing the actuator, which moves the end portion of the light-transmitting member, the collimator optical system, or the pupil-projection optical system in the optical-axis direction, parallel to a plane including the optical axes before and after deflection, the actuator is prevented from protruding in the width direction, which reduces the projecting area on the subject; thus, an advantage is afforded in that it is possible to observe the subject from the opposite side of the focusing optical system from the subject, for example, such that it does not obstruct the stereomicroscope observation.

Moreover, according to the present invention, by separating the objective unit from the apparatus main body and keeping it inserted in the living organism, it is possible to perform observation without shifting the objective unit relative to the examination site when performing multiple observations of the same examination site of the living organism over time. Also, when attaching the apparatus main body to an objective unit remaining in the living organism, it is not necessary to rotate the objective unit, which allows the burden placed on the living organism to be reduced. Therefore, an advantage is afforded in that it is possible to perform in-vivo examination of biological tissue, such as cells or muscles, or various internal organs, such as the heart or liver, of mammals, including small laboratory animals, over a relative long period of time.

BEST MODE FOR CARRYING OUT THE INVENTION

An optical-scanning microscope examination apparatus according to an embodiment of the present invention is described below with reference to FIGS. 1 to 3.

Figure 1:
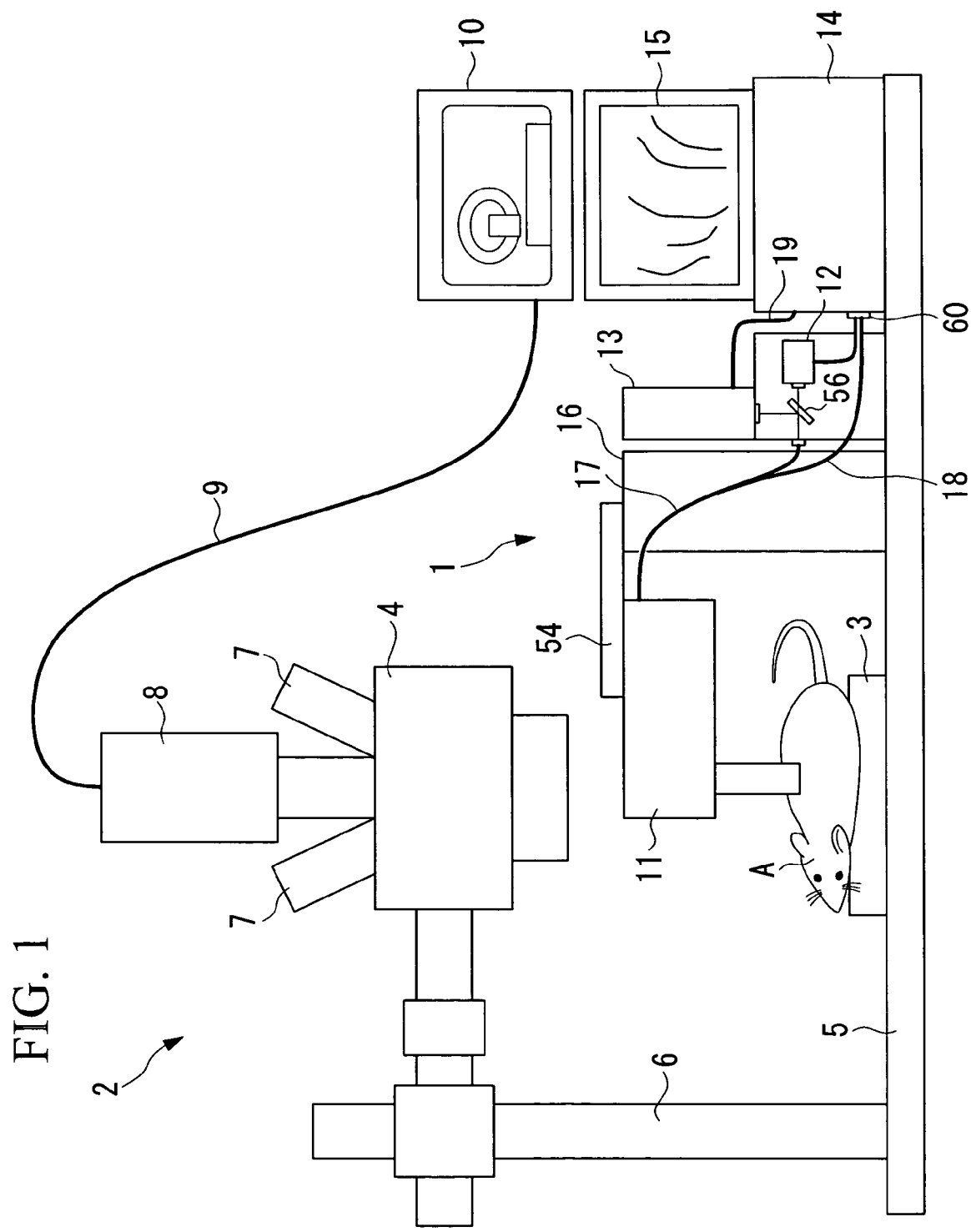
FIG. 1 is a diagram showing, in outline, a microscope examination system including a scanning microscope examination apparatus according to a first embodiment of the present invention.

An optical-scanning microscope examination apparatus 1 according to this embodiment is used in a microscope examination system 2 shown in FIG. 1. As shown in FIG. 1, this microscope examination system 2 includes a stage 3 for mounting a subject, such as a small laboratory animal; the optical-scanning microscope examination apparatus 1 according to this embodiment, which is disposed above the stage 3; and a stereomicroscope examination apparatus 4, which is disposed further thereabove.

The stereomicroscope examination apparatus 4 is disposed on a support stand 6, which rises from a base 5 including the base 3, in such a manner as to be capable of moving upward and downward and includes eyepieces 7 and a CCD camera 8 for observing the subject A at comparatively low magnification. The CCD camera 8 is connected to a first monitor 10 via a cable 9 so as to allow observation of the acquired image on the first monitor 10.

As shown in FIG. 1, the optical-scanning microscope examination apparatus 1 according to this embodiment includes a microscope examination apparatus main body 11, and a light source 12, a light detector 13, a control apparatus 14, and a second monitor 15 connected thereto.

The microscope examination apparatus main body 11 is also disposed so as to be capable of moving upward and downward on a support stand 16, which rises from the base 5, and so as to be capable of tilting at an arbitrary angle. The microscope examination apparatus main body 11 and the light source 12 are connected via an optical fiber (light-transmitting member) 17. Also, the microscope examination apparatus main body 11 and the control apparatus 14, and the light detector 13 and the control apparatus 14, are connected via cables 18 and 19, respectively. The second monitor 15 displays an image that has been subjected to image processing in the control apparatus 14.

Figure 2:
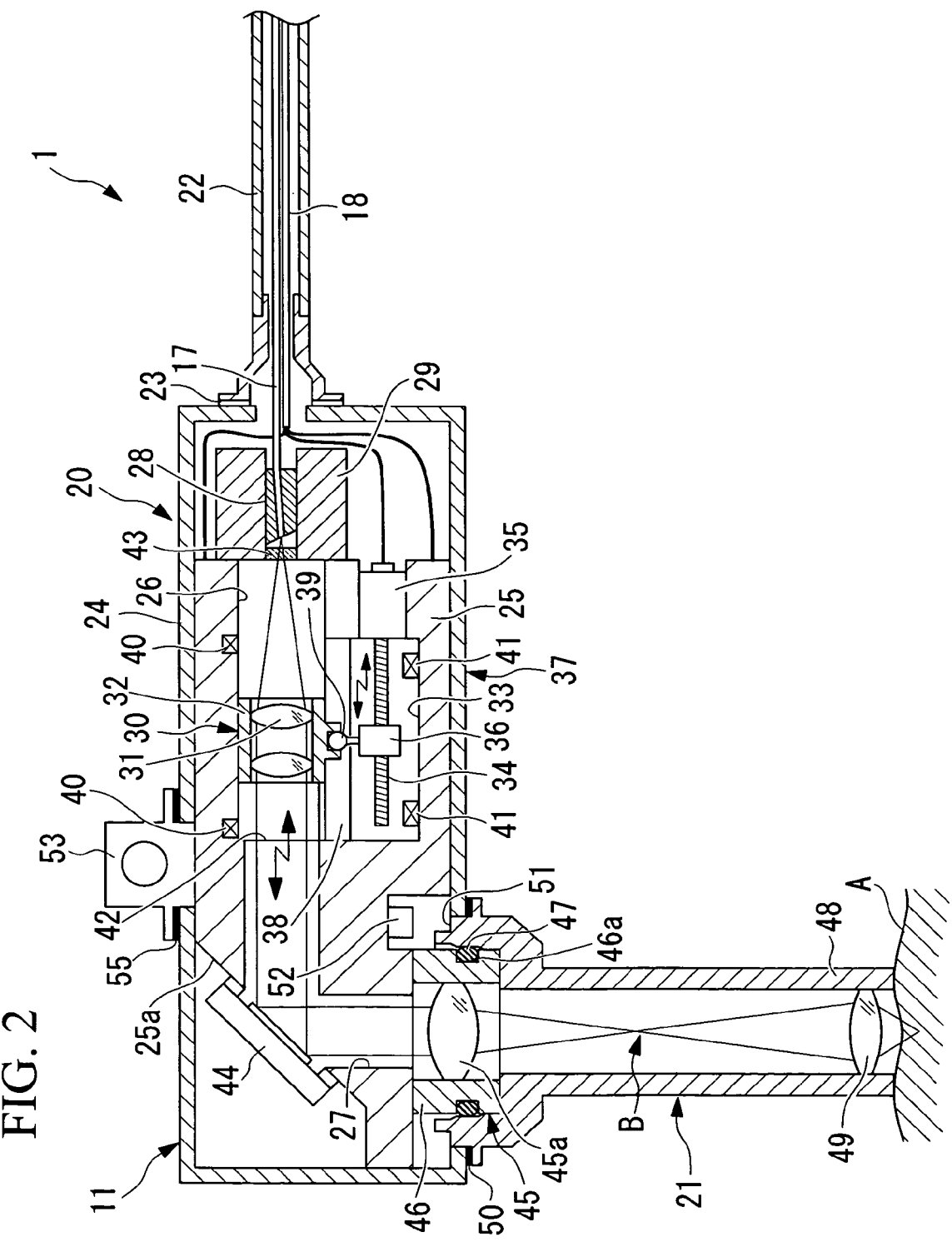
FIG. 2 is a longitudinal sectional diagram showing the detailed construction of the scanning microscope examination apparatus according to the first embodiment of the present invention.

As shown in FIG. 2, the microscope examination apparatus main body 11 includes a chassis 20 which is attached to one end of the optical fiber 17 and an objective lens unit (focusing optical system) 21 which is attached to the chassis 20. The optical fiber 17 is covered by a sheath 22. An opening at the end of the sheath 22 and the chassis 20 are tightly connected by a watertight seal 23. A cable 18 is wired inside the sheath 22 for connecting each of the devices inside the microscope examination apparatus main body 11, for example, a galvanometer mirror unit described below, a stepping motor, a code reader, and so on, to the control apparatus 14.

The chassis 20 is formed of a cover member 24 and a base member 25 which is secured in the interior thereof. The base member 25 functions as a base for securing various members to be described later or for supporting them in a slidable manner.

The base member 25 is a substantially rectangular-block-shaped member and includes a first through-hole 26 passing through in the longitudinal direction thereof and a second through-hole 27 orthogonal to the first through-hole 26. A ferrule 28 to which the end of the optical fiber 17 is attached is secured in an opening at the end of the first through-hole 26 by a bracket 29. By cutting the end surface at an angle, the ferrule 28 is configured so that an light-emitting end surface of the optical fiber 17 is formed at an angle relative to the longitudinal direction, which prevents light reflected at the emission end surface inside the optical fiber 17 from returning to the light detector 13 (described later).

A collimator lens unit 30 is supported inside the first through-hole 26 in the base member 25 in such a manner as to be capable of moving in the longitudinal direction of the first through-hole 26. The collimator lens unit 30 contains one or more collimator lenses 31 inside a lens barrel 32.

The base member 25 also contains an actuator 37 formed of a lead screw 34 which extends parallel to the first through-hole 26 inside a hole 33 formed parallel to the first through-hole 26; a stepping motor 35 which rotates the lead screw 34 about a longitudinal axis; and a nut 36 which is threaded on the lead screw 34 and is linearly translated in a direction along the first through-hole 26 by the rotation of the lead screw 34.

Other driving mechanisms may be used instead of the stepping motor, such as a DC motor with an encoder.

The hole 33 and the first through-hole 26 communicate with each other via a communicating portion 38, and the nut 36 and the lens barrel 32 are connected by a connecting portion formed of a spherical bearing 39. In other words, by virtue of the spherical bearing 39, the lens barrel 32 and the nut 36 are connected so as to have a rotational degree of freedom about an axis orthogonal to the longitudinal direction of the first through-hole 26. That is, even if some play occurs between the first through-hole 26 and the lead screw 34, they are constructed so that no substantial internal force is exerted on the first through-hole 26 and the lens barrel 32. A rotation stop for the spherical bearing 39 is formed of a groove (not shown in the drawing) provided in the base member 25 along the longitudinal direction of the first through-hole 26.

Movement-range detectors 40 for detecting the lens barrel 32 are provided in the first through-hole 26, at both ends of the range of movement of the lens barrel 32. In addition, movement-range detectors 41 for detecting the nut 36 are provided inside the hole 33 containing the lead screw 34, at both ends of the movement range of the nut 36. It is also possible to provide just one of these movement-range detectors 40 and 41.

An abutting surface 42 against which the end face of the lens barrel 32 abuts is provided at one end of the first through-hole 26. Continuously rotating the lead screw 34 in one direction, by operating the stepping motor 35, to make it rotate further from the state where the end surface of the lens barrel 32 abuts against the abutting surface 42 can cause the stepping motor 35 to go out of synchronization. Thus, it is possible to correctly reset the origin position by rotating the lead screw 34 thereafter in the reverse direction by a predetermined rotational angle.

Transparent glass 43 which separates the ferrule 28 and the collimator lens unit 30 and which allows light to be transmitted is disposed in the bracket 29 which connects the ferrule 28 to the base member 25. Although it is conceivable that dust is produced by sliding the collimator lens unit 30 inside the first through-hole 26, it is provided so that the dust produced does not adhere to the ferrule 28.

In this embodiment, the actuator 37, which linearly translates the collimator lens unit 30 in the longitudinal direction of the first through-hole 26, is disposed in a space formed on a plane parallel to the central axis of the first through-hole 26 and the central axis of the second through-hole 27. In other words, when the chassis 20 is disposed above the objective lens unit 21, the lead screw 34, the nut 36, and the stepping motor 35 are located below the first through-hole 26 so as not to protrude in the lateral direction. As a result, it is possible to reduce the dimensions of the chassis 20, and thus, the projecting area from above onto the subject A is small, and it does not block the field of view of the stereomicroscope examination apparatus 4 which is disposed thereabove.

The base member 25 has a tilted face 25a that forms an angle of 45° relative to the axes of the through-holes 26 and 27 close to the intersection of the first through-hole 26 and the second through-hole 27. A galvanometer mirror unit (beam scanning unit, deflecting mechanism) 44 which is capable of two-dimensional scanning is secured to this tilted face 25a in such a manner that it blocks the through-holes 26 and 27. Accordingly, a laser beam coming through the first through-hole 26 is deflected by substantially 90° by the galvanometer mirror unit 44 to be guided inside the second through-hole 27.

A scanning mechanism which is driven by a piezoelectric element, a polygon mirror, or the like may be used instead of the galvanometer mirror.

A pupil-projection lens unit 45 having a pupil-projection lens 45a is fixed in an opening at the end of the second through-hole 27a by a bracket 46. The pupil-projection lens unit 45 images the laser beam deflected by the galvanometer mirror unit 44 at an intermediate image position B at one end. Accordingly, divergence of off-axis rays of the laser beam is prevented, thus reducing the beam diameter and allowing it to pass through the interior of the elongated objective lens unit 21.

A circumferential groove 46a is formed around the entire circumference in the outer circumferential surface of the bracket 46 of the pupil-projection lens unit 45, and an O-ring 47 is disposed inside the circumferential groove 46a.

The objective lens unit 21 includes a substantially cylindrical lens barrel 48 which is mated with the outer surface of the bracket 46 of the pupil-projection lens unit 45, and one or more objective lenses 49 is contained inside. The objective lens 49 is constructed so as to re-image the intermediate image formed by the pupil-projection lens unit 45 at the subject A.

The lens barrel 48 and the bracket 46 are watertightly sealed by the O-ring 47 therebetween. The lens barrel 48 and the cover member 24 of the chassis 20 are also sealed by a watertight seal 50 therebetween.

At the end face which mates to the bracket 46 of the lens barrel 48, a code portion 51 formed by cutting out a part thereof is provided. When there are a plurality of objective lens units 21, this code portion 51 has a fixed shape for each objective lens unit 21. When the objective lens unit 21 is mated with the bracket 46, a code detector 52 for reading this code portion 51 is disposed on the base member 25 at a position opposite the code portion 51.

A contact/non-contact sensor (not shown in the drawing) may be provided inside the chassis 20 for detecting contact/non-contact with the objective lens unit 21.

By deflecting the light in this way with the galvanometer mirror unit 44, when the objective lens unit 21 is positioned in the vertical direction, the first through-hole 26 is disposed substantially horizontally, and therefore, it is possible to reduce the length from the tip of the objective lens unit 21 to the upper end of the chassis 20. As a result, it is possible to reduce the length from the stereomicroscope examination apparatus 4 positioned above the chassis 20 to the subject A.

Reference numeral 53 in the drawing is an attaching portion for securing the examination apparatus main body 11 to an arm 54 that extends from the support stand 16; this attaching portion 53 is also secured to the base member 25 and is sealed to the cover member 24 with a watertight seal 55 therebetween.

The light source 12 is, for example, a laser light source which can selective emit excitation light of a plurality of wavelengths. A selection mechanism for selecting the wavelength of the light source 12 is included in the control apparatus 14. The light detector 13, which is a photomultiplier tube (PMT), for example, is constructed so as to detect fluorescence split off from the return light by a dichroic mirror 56 inside the light source 12 and input it to the control apparatus 14 as an image signal.

Figure 3:
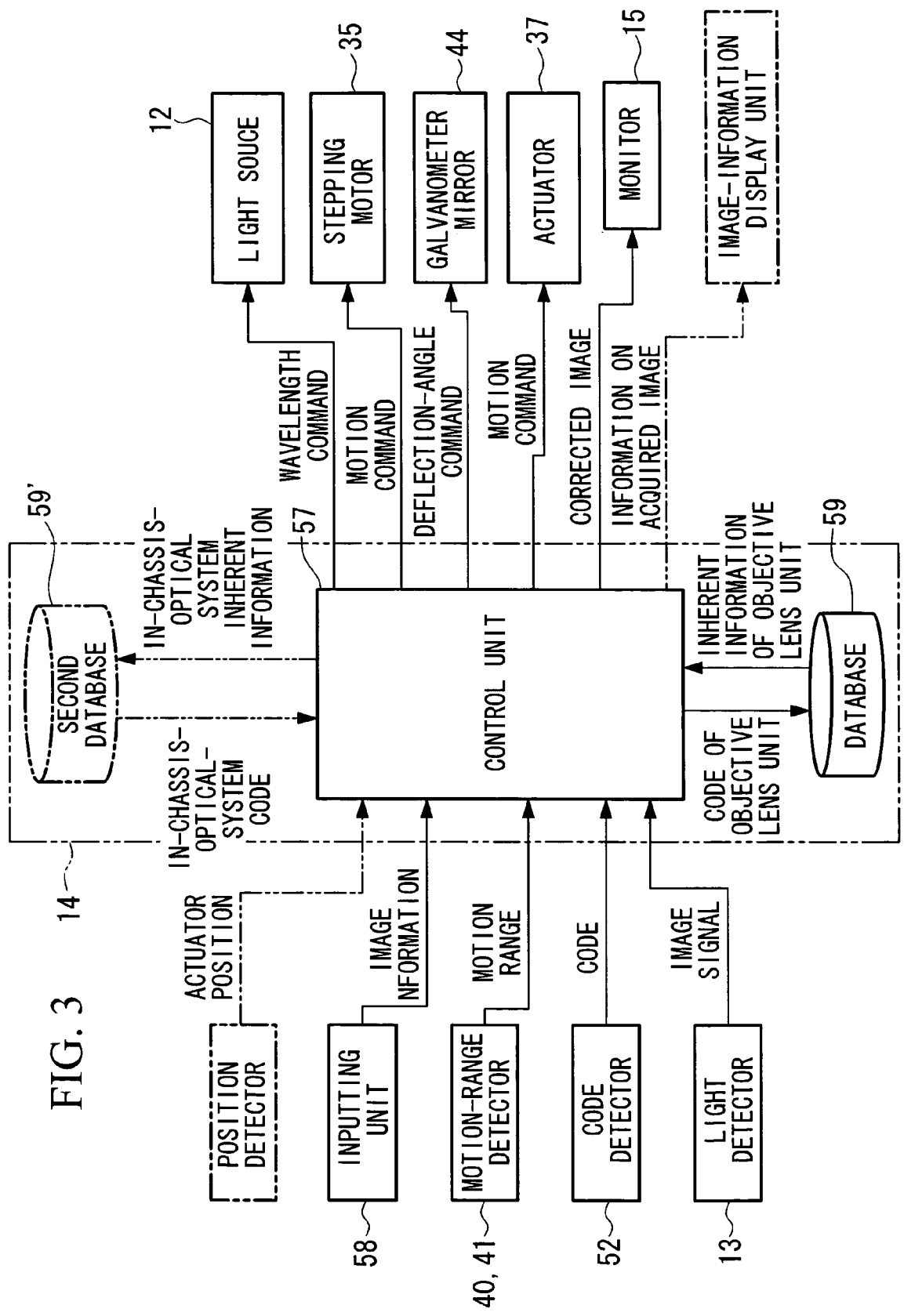
FIG. 3 is a block diagram showing the function of a control apparatus in the scanning microscope examination apparatus in FIG. 2.

As shown in FIG. 3, the control apparatus 14 outputs to the light source 12 an instruction for changing the wavelength of the light to be emitted. It includes a control unit 57 for outputting a motion command to the stepping motor 35 of the examination apparatus 11 and for outputting a deflection-angle command to the galvanometer mirror unit 44. Output signals from the movement-range detectors 40 and 41 and the code-portion detector 52 are input from the microscope examination apparatus main body 11. Furthermore, acquired image information is input from the light detector 13.

An inputting unit 58, for example, a keyboard, mouse, or joystick, is connected to the control apparatus 14, which allows image information about the acquired image, for example, the image magnification, the depth position of the image, the field of view of the image, or the frame rate, to be input. Then, the control apparatus 14 calculates motion commands for the actuator 37 based on the input image information.

A database 59 is provided in the control apparatus 14. The database 59 stores, in an associated fashion, the codes indicated by the code portions 51 of all objective lens units 21 used; and information inherent to the objective lens units 21, for example, the nominal magnifications of the objective lens units 21, the intrinsic magnifications, the magnification errors, magnification characteristic functions representing the relationship between the wavelength of the light and the magnification, aberration characteristic functions representing, for each type of aberration, the relationship between the wavelength of the light and the aberration, serial numbers of the objective lens units 21, and so forth.

The aberration characteristic function representing, for each type of aberration, the relationship between the wavelength of the light and the aberration is information about the aberration characteristics of the objective lens unit 21, for each wavelength. For example, regarding distortion, because there are various types for each objective lens, such as "pincushion" and "barrel", information about the type of distortion and correction values therefor in the individual objective lens units 21 are held in the database 59 as inherent information. The correction values are set to be variable for each wavelength.

Based on the code of the objective lens unit 21 read by the code detector 52, each type of corresponding inherent information is read out, and it is possible to use it to calculate the image information, as well as the motion commands for the actuator 37.

The control apparatus 14 is provided with a function for correcting the image signal obtained by the light detector 13 based on the aberration characteristic function read out. The corrected image signal that is corrected is output to the second monitor 15.

The operation of the scanning microscope examination apparatus 1 according to this embodiment, having such a configuration, will be described below.

To examine the subject A using the microscope examination system 2 described above, first, the subject A, such as a small laboratory animal or the like, including a mouse or a rat, is secured to the stage 3, and while displaying an image of the examination site on the first monitor 10 using the stereomicroscope examination apparatus 4 disposed thereabove, the skin is incised to expose the internal organs. At this time, the microscope examination apparatus main body 11 of the scanning microscope examination apparatus 1 is disposed at a position away from the field of view of the stereomicroscope examination apparatus 4.

In the scanning microscope examination apparatus 1, the objective lens unit 21 used for achieving the desired observation magnification is attached to the chassis 20. The objective lens unit 21 and the chassis 20 are sealed with the O-ring 47 and the watertight seal 50 so that water cannot enter the interior. When the objective lens unit 21 is attached to the chassis 20, the code indicated by the code portion 51 provided on the objective lens unit 21 is read by the code detector 52 and sent to the control apparatus 14. In the control apparatus 14, the database 59 is searched using the sent control code as a key, and the information inherent to that objective lens unit 21 is read out.

Once preparations have been completed, the microscope examination apparatus main body 11 of the scanning microscope examination apparatus 1 is inserted between the stereomicroscope examination apparatus 4 and the subject A.

With the scanning microscope examination apparatus 1 according to this embodiment, the actuator 37 for changing the position of the collimator lens unit 30 is disposed parallel to a plane including the first through-hole 26 and the second through-hole 27, and the width dimension thereof is set sufficiently small. Therefore, it is possible to carry out high-magnification examination with the scanning microscope examination apparatus 1 while continuously observing the examination site with the stereomicroscope examination apparatus 4, without substantially blocking the field of view of the stereomicroscope examination apparatus 4.

Because the first through-hole 26 and the second through-hole 27, which guide the light, are disposed to form an angle of 90° between each other by means of the galvanometer mirror unit 44, when the second through-hole 27 and the objective lens unit 21 which is contiguous therewith are disposed vertically, it is possible to dispose the first through-hole 26 substantially horizontally. Therefore, because the laser light irradiating the subject A can be guided from the side rather than being guided from directly above, it is possible to reduce the dimension in the height direction. Accordingly, it is possible to reduce the distance between the stereomicroscope examination apparatus 4 and the subject A.

Therefore, the tip of the objective lens unit 21 provided in the microscope examination apparatus main body 11 presses against the exposed examination site of the subject A. Accordingly, even if the subject A exhibits pulsing, the movement of the examination site can be suppressed by the tip of the objective lens unit 21, which allows image blurring to be prevented.

The control apparatus 14, the light source 12, and the light detector 13 are operated in this state, and based on the image information input from the inputting unit 58, the control apparatus 14 outputs a wavelength command for the light source 12, a motion command for the actuator 37, and a deflection-angle command for the galvanometer mirror unit 44.

When the wavelength command for the light source 12 is sent to the light source 12, the specified wavelength is set by a wavelength-adjusting mechanism, which is not shown in the drawing, so as to output laser light.

The laser light emitted from the light source 12 propagates through the optical fiber 17 to the interior of the chassis 20 of the microscope examination apparatus main body 11. The top of the optical fiber 17 is fixed to the base member 25 inside the chassis 20 by the ferrule 28, and the laser light is emitted from the end surface thereof towards the first through-hole 26. Since the end surface of the optical fiber 17 is cut at an angle, light reflected at the end surface can be prevented from returning through the optical fiber 17 and being detected by the light detector 13.

The laser light issuing from the tip of the optical fiber 17 is converted to a collimated beam upon being transmitted through the collimator lens unit 30, and is incident on the galvanometer mirror unit 44. Because the galvanometer mirror unit 44 is disposed so as to form an angle of 45° with respect to the optical axis of the collimator lens unit 30, the incident light from the collimator lens unit 30 is deflected by 90° and output. The galvanometer mirror unit 44 two-dimensionally scans the laser light in response to the deflection-angle command from the control apparatus 14. Accordingly, when the deflected laser light is transmitted through the pupil-projection lens unit 45 and the objective lens unit 21 and irradiates the subject A, it is two-dimensionally scanned and irradiates the subject A over a field of view input by the inputting unit 58.

The laser light deflected at the galvanometer mirror unit 44, after forming the intermediate image by the pupil-projection lens unit 45, is re-imaged at the subject A by the objective lens unit 21. When the laser light irradiates the subject A, fluorescence is produced in the subject A, and the produced fluorescence returns along the same optical path via the objective lens unit 21, the pupil-projection lens unit 45, the galvanometer mirror unit 44, the collimator lens unit 30, and the optical fiber 17, is split off from the laser light by the dichroic mirror 56, and is detected by the light detector 13.

When the motion command for the actuator 37 is sent to the stepping motor 35, the nut 36 is made to move in the direction along the first through-hole 26 by rotating the lead screw 34 by the instructed rotation angle. When the nut 36 is moved, the lens barrel 32, which is connected to the nut 36, is made to move, and the focal position of the laser light at the tip of the objective lens unit 21 is adjusted by making the internal collimator lens 31 move together with the lens barrel 32.

When the observation magnification of the scanning microscope examination apparatus 1 changes, the magnification is input from the inputting unit 58. The amount of movement of the actuator 37 for achieving the input magnification is calculated again in the control apparatus 14, and the motion command is sent to the stepping motor 35. Accordingly, the collimator lens unit 30 is moved in the optical-axis direction, and the focal position of the laser light at the tip of the objective lens unit 21 is changed.

In such a case, with the scanning microscope examination apparatus 1 of this embodiment, to calculate the motion command for the actuator 37, the inherent information of the objective lens unit 21, which is read out from the database 59, is used. In other words, the magnification of the objective lens unit 21 differs from the nominal magnification due to individual differences in the optical components, such as each of the lenses 49 constituting the objective lens unit 21, and by reading out that information from the database 59, it is reflected in the generation of the motion command for the actuator 37. Accordingly, even if the objective lens unit 21 is replaced, normally, it is possible to generate motion commands which reflect the individual differences of the objective lens units 21, and it is thus possible to realize the specified magnification precisely.

When setting and changing the focal position, it is achieved merely by moving the collimator lens unit 30 inside the chassis 20, without moving the tip of the objective lens unit 21, and therefore, it is possible to continuously carry out examination while keeping the pulsing of the subject A suppressed. Therefore, it is possible to acquire a clear, blur-free image.

Because the nut 36 of the actuator 37, which moves the collimator lens unit 30, is connected to the lens barrel 32 of the collimator lens unit 30 by the spherical bearing 39, it is possible to mutually rotate the collimator lens unit 30 and the lens barrel 32 about an axis orthogonal to the optical axis. As a result, even if there are errors in connecting the lens barrel 32 to the chassis 20 or connection errors between the lens barrel 32 and the nut 36, by making the collimator lens unit 30 and the lens barrel 32 mutually rotate, it is possible to absorb such connection errors.

In the scanning microscope examination apparatus 1 according to this embodiment, the inherent code is indicated on the objective lens unit 21 by the notch 51 provided on the objective lens unit 21; instead of this, however, another code may be employed. Moreover, instead of the database 59 connected to the control apparatus 14, an IC chip storing the inherent information may be provided in the objective lens unit 21 itself.

Using the code is advantageous in that inherent errors in the individual components involved in size reduction of the mechanical components and optical components are corrected, which allows the desired image to be acquired and correct image information to be displayed.

The placement of the actuator 37 is not limited to that in the embodiment described above. In general, an optical-scanning microscope having a light source, a light-transmitting member, a collimator optical system, a beam-scanning unit, a focusing optical system, a pupil-projection optical system, a light detector, an actuator, and a control apparatus and using a compact, small-diameter focusing optical system is effective.

It is also acceptable to provide a connector 60 for connecting a code (an in-chassis optical-system code) indicating inherent information, such as the magnification or aberrations of the pupil-projection lens unit 45 and the collimator lens unit 30 provided inside the microscope examination apparatus main body 11, to the control apparatus 14, for example, and to provide a reader therefor (not shown in the drawing) in the control apparatus 14. Moreover, as the key for the read code, the control apparatus 14 may be provided with another database (second database) 59' that can be searched for the associated inherent information.

Figure 4:
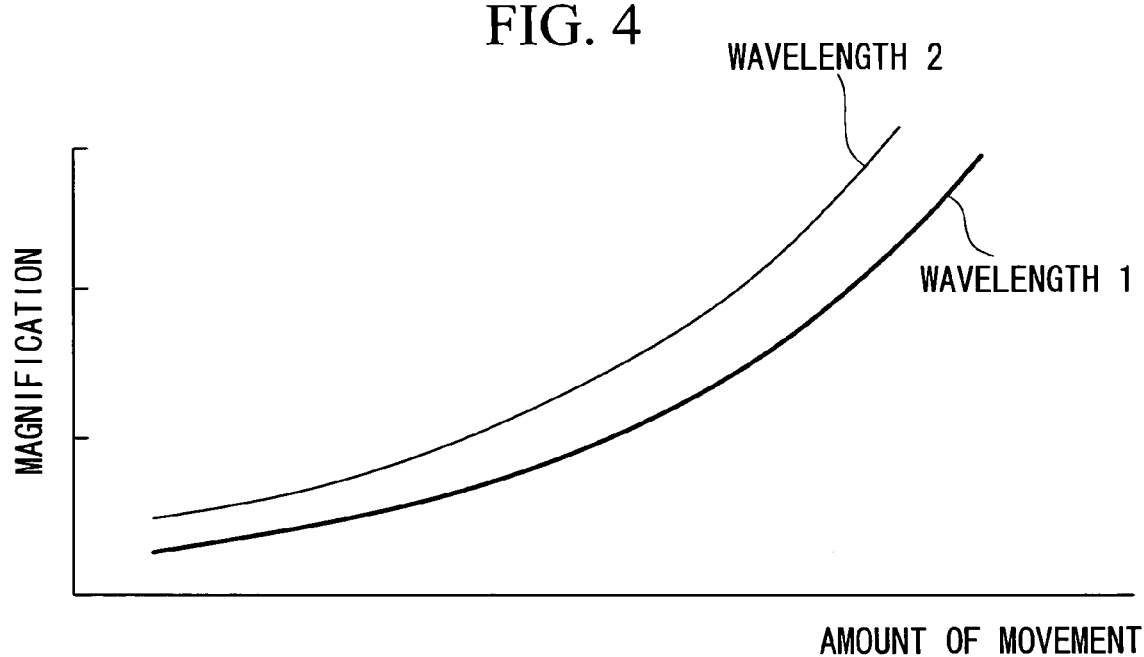
FIG. 4 is a graph showing one example of the characteristics of a collimator lens unit used in the control apparatus of the scanning microscope examination apparatus in FIG. 2.

In such a case, as shown in FIG. 4, an image characteristic or the like indicating the relationship between the amount of movement and the magnification for the collimator lens unit 30 or the pupil-projection lens unit 45 may be included as the corresponding inherent information. Then, by calculating the motion command for the actuator 37 based on the searched inherent information, and also in light of the individual differences in the pupil-projection lens units 45 and the collimator lens units 30, it is possible to realize input image information with good precision.

Figure 5:
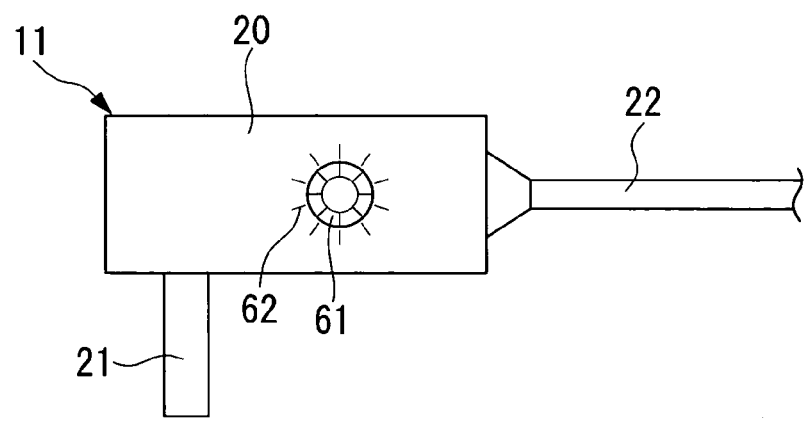
FIG. 5 is a side view showing a first modification of an inputting unit of the scanning microscope examination apparatus in FIG. 2.
Figure 6:
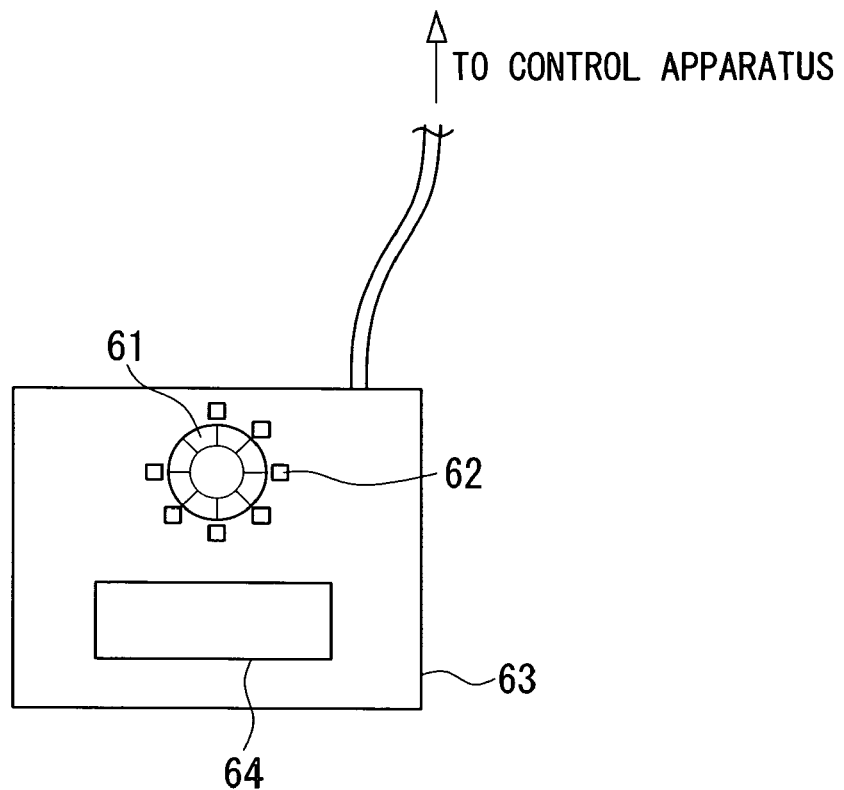
FIG. 6 is a diagram showing a second modification of the inputting unit of the scanning microscope examination apparatus in FIG. 2.

In the embodiment described above, the image information to be obtained is input using an input device such as a keyboard (not shown in the drawing) provided in the control apparatus 14; instead of this, however, as shown in FIG. 5, a dial 61 and a scale 62 for inputting the image information, for example, the magnification, may be provided on the side of the chassis 20. The operator can set the image information using the dial 61 while operating the microscope examination apparatus main body 11, and the setting is thus simple. As shown in FIG. 6, the dial 61 and the scale 62 may be provided on a controller 63 that is connected to the control apparatus 14 instead of on the microscope examination apparatus main body 11. Reference numeral 64 in the drawing is a liquid crystal screen for displaying the set value.

Figure 7:
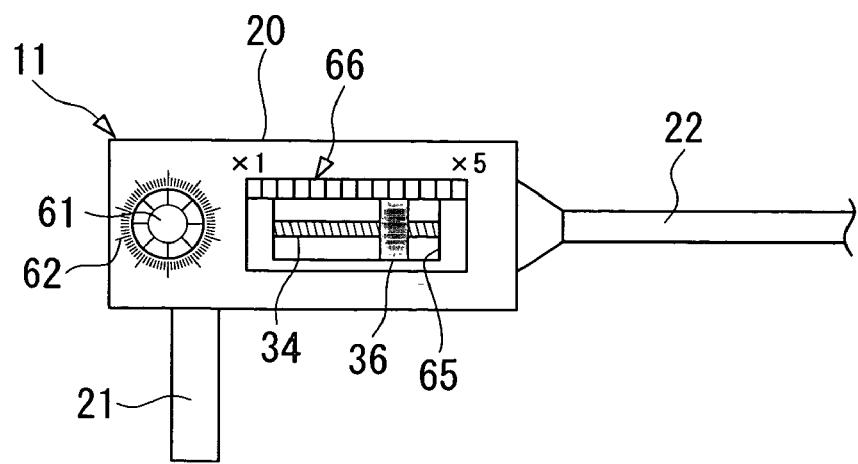
FIG. 7, which is a modification of the scanning microscope examination apparatus in FIG. 2, is a side view showing a case where there is a window for displaying image information.

As shown in FIG. 7, a window 65 for exposing the nut 36 of the internal actuator 37 may be provided in the side face of the chassis 20, and a scale 66 may be provided at the edge of the window 65 for indicating the current magnification using the position of the nut 36.

Figure 8:
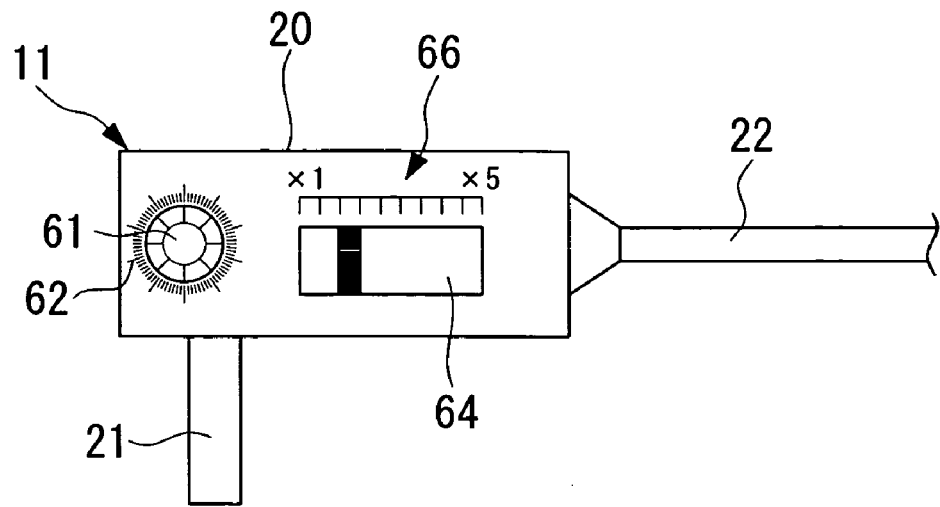
FIG. 8, which is a modification of FIG. 7, is a side view showing a case where there is a liquid crystal screen for displaying the image information.

As shown in FIG. 8, the liquid crystal screen 64 and the scale 66, which is disposed at the edge thereof, may be provided on the side of the chassis 20 for displaying the magnification, which changes depending on the position of the collimator lens unit 30, on the liquid-crystal screen 64. In this case, an encoder for detecting the position of the nut 36 of the actuator 37 may be incorporated and the detection result thereof displayed on the liquid-crystal screen 64.

Figure 9:
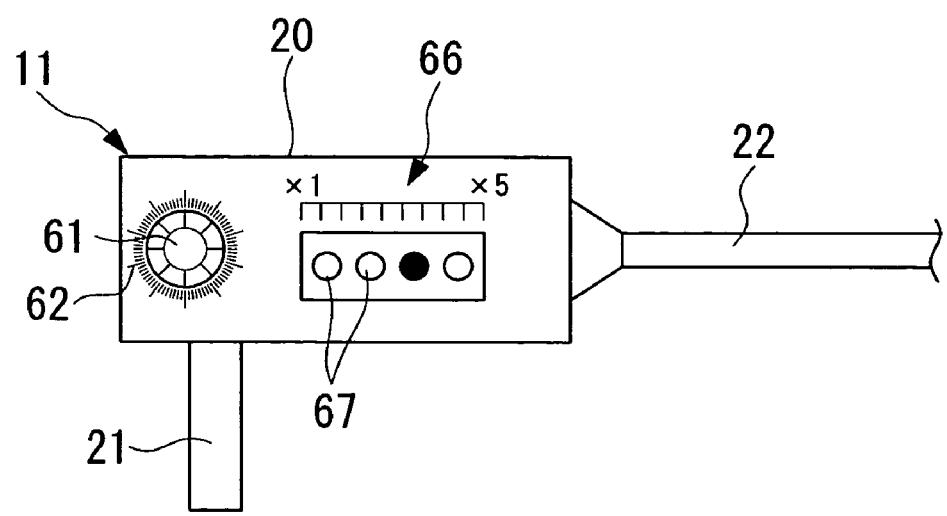
FIG. 9, which is a modification of FIG. 7, is a side view showing a case where there is an LED array for displaying the image information.

As shown in FIG. 9, instead of the liquid-crystal display, the magnification may be displayed using an array of LEDs 67.

Figure 14B:
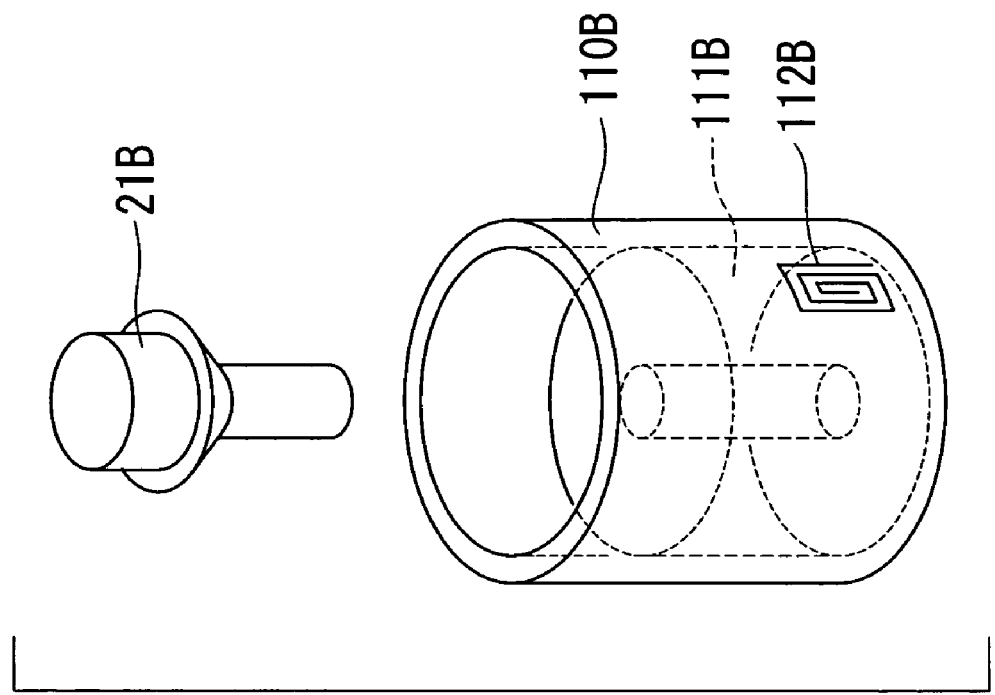
FIGS. 14 A and B are perspective views showing examples of a storage container provided with a code.
Figure 14A:
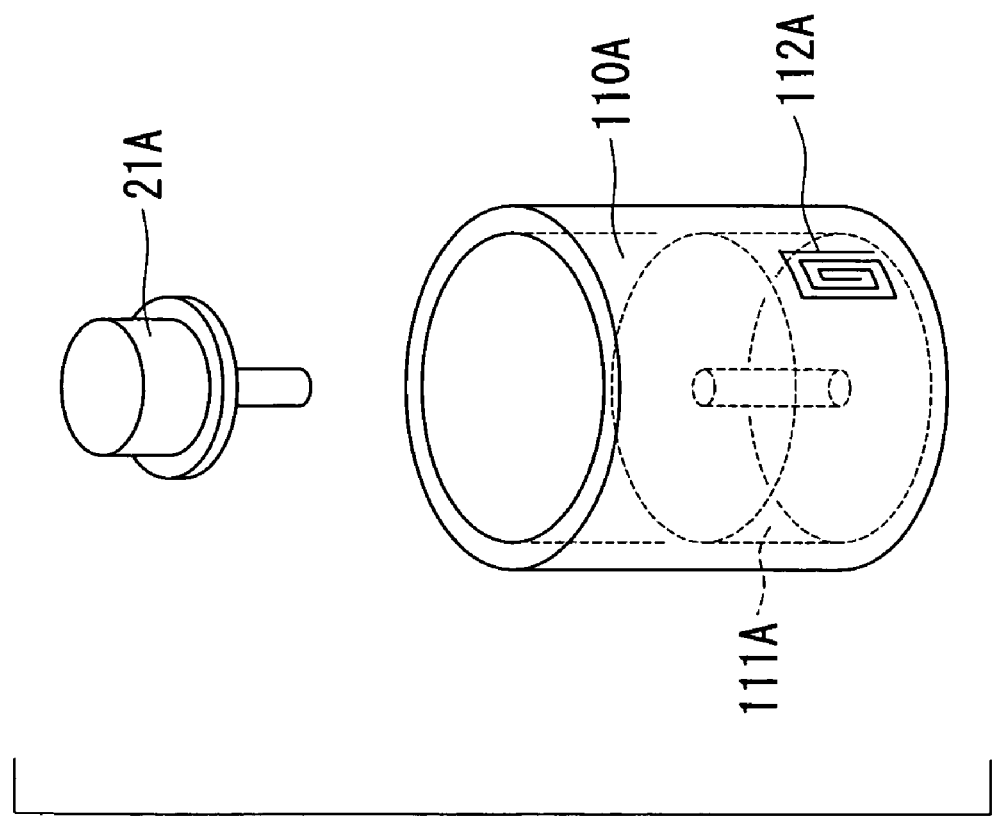

Instead of providing the code or IC chip in the objective lens unit 21, as shown in FIGS. 14 A and 14 B, storage containers 110A, 110B, etc. which contain objective lens units 21A, 21B, etc. may be provided, and codes 112A, 112B, etc. may be attached to the storage containers 110A, 110B, etc. It is possible to record information about the magnification, numerical aperture, corresponding wavelength range, and observation atmosphere of the objective lens units 21A and 21B in the codes 112A and 112B. By doing so, even if codes cannot be attached to the objective lens units 21A, 21B, etc. because they are extremely small, using the storage containers 110A, 110B, etc. is advantageous in that sufficient space can be ensured. Also, if the objective lens units 21A and 21B are attached in advance to a living organism, an advantage is afforded in that it is possible to read out the codes 112A and 112B using the storage containers 110A and 110B, which are separate from the objective lens units 21A and 21B.

In this case, it is preferable to dispose holding members 111A and 111B, which are capable of containing only the corresponding objective lens unit 21A and 21B, inside the storage containers 110A and 110B. In the example shown in FIGS. 14 A and 14 B, the holding members 111A and 111B are constituted of cylindrical members having through-holes matching the outer diameters of the objective lens units 21A and 21B.

Figure 10:
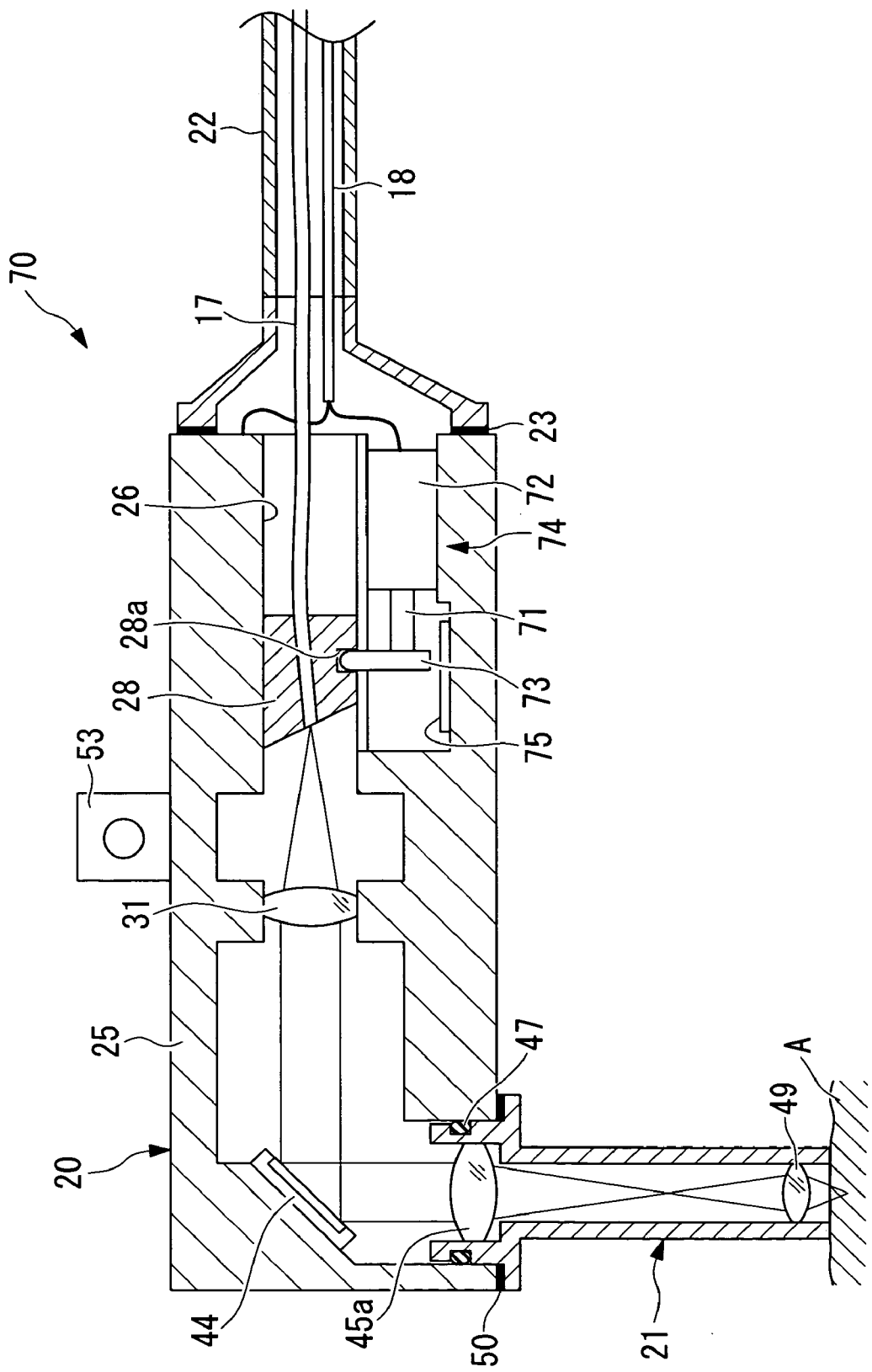
FIG. 10 is a longitudinal sectional diagram showing the detailed construction of a scanning microscope examination apparatus according to a second embodiment of the present invention.

Next, a scanning microscope examination apparatus 70 according to a second embodiment of the present invention will be described below with reference to FIG. 10.

In the description of this embodiment, parts having the same configuration as those in the scanning microscope examination apparatus 1 according to the first embodiment described above are assigned the same reference numerals, and a description thereof is omitted.

The scanning microscope examination apparatus 70 according to this embodiment differs from the first embodiment in that, whereas the scanning microscope examination apparatus 1 according to the first embodiment moves the collimator lens unit 30, the ferrule 28 (end portion of the light-transmitting member) to which the end of the optical fiber 17 is secured is moved in the optical-axis direction.

The ferrule 28 is disposed in such a manner that it can slide inside the first through-hole 26. In addition, an actuator 74 formed of a rod 71, a plunger 72 that makes the rod 71 project in the optical-axis direction, and a connecting member 73 connected to the rod 71 of the plunger 72 are provided. By engaging the connecting member 73 with a groove 28a provided in the ferrule 28, the linear translation of the rod 71 is transmitted as a linear translation of the ferrule 28. An encoder 75 disposed along the direction of that motion is provided close to the connecting member 73, and the position of the ferrule 28 in the rectilinear direction is detected by the encoder 75.

The collimator lens unit 30, which is provided in the first embodiment in such a manner as to be capable of moving, is fixed inside the base member 25 of the chassis 20.

With the scanning microscope examination apparatus 70 according to this embodiment, having such a configuration, as in the first embodiment, it is possible to move the focal position without moving the end surface of the objective lens unit 21, but keeping it abutting against the subject A.

Because the ferrule 28 is lighter than the collimator lens unit 30, and is thus easy to move with the actuator 74, an advantage is provided in that it is easy to adjust the focal position.

Figure 11:
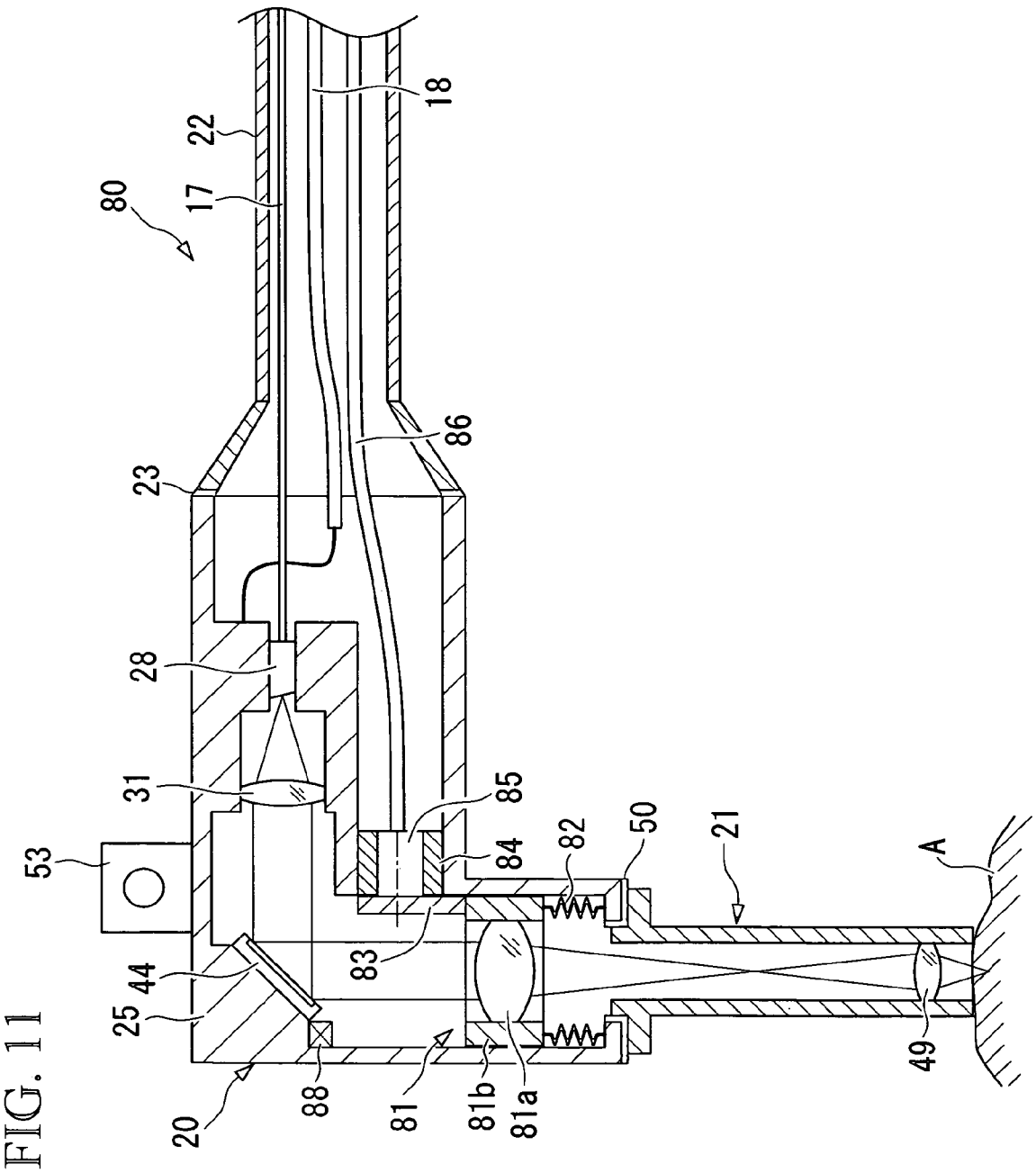
FIG. 11 is a longitudinal sectional diagram showing the detailed construction of a scanning microscope examination apparatus according to a third embodiment of the present invention.
Figure 12:
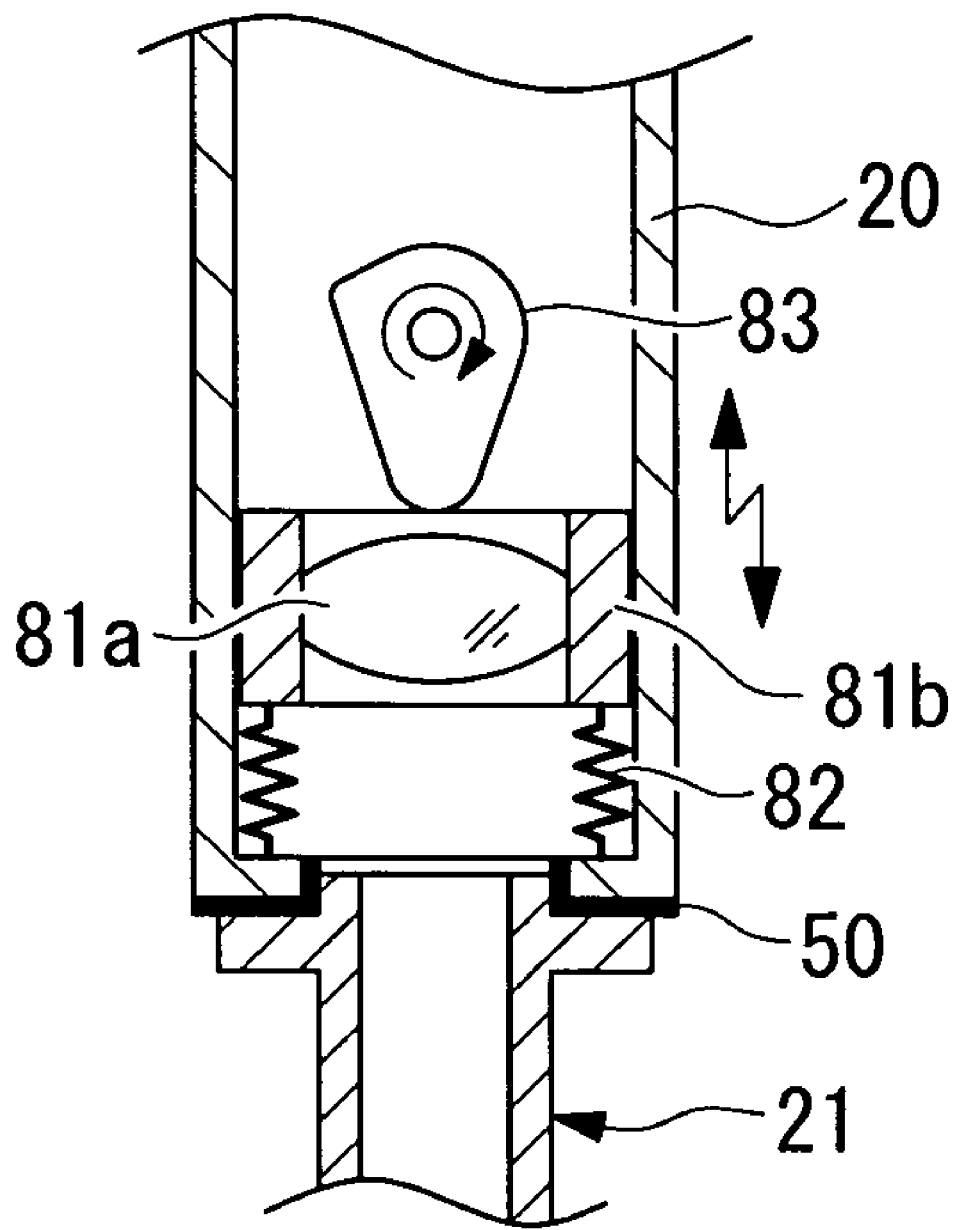
FIG. 12 is a longitudinal sectional diagram showing a cam 83 for moving a pupil-projection lens 81a in the scanning microscope examination apparatus in FIG. 11.

Next, a scanning microscope examination apparatus 80 according to a third embodiment of the present invention will be described below with reference to FIGS. 11 and 12.

In the description of this embodiment, parts having the same configuration as those of the scanning microscope examination apparatus 1 and 70 according to the second embodiment are assigned the same reference numerals, and a description thereof is omitted.

Whereas the scanning microscope examination apparatuses 1 and 70 according to the first and second embodiments move the collimator lens unit 30 or the ferrule 28 in the optical axis direction, in the scanning microscope examination apparatus 80 according to this embodiment, the collimator lens unit 30 and the ferrule 28 are fixed to the chassis 20, and a pupil-projection lens unit 81 is moved along the optical-axis direction.

The pupil-projection lens unit 81, in which a lens barrel 81b, including a pupil-projection lens 81a, is disposed in such a manner as to be capable of sliding inside the chassis 20, is always urged upward by means of a compression spring 82 disposed therebelow. Thus, by disposing it above the lens barrel 81*b* and in close contact with the upper surface of the lens barrel 81*b* and by rotating it about the horizontal axis, a cam 83 which exerts a force in a direction that presses down on the lens barrel 81*b* from above according to the rotation angle thereof is provided. The cam 83 is rotated by a rotating body 85, which is supported in a freely rotatable manner by a sliding bearing 84, and a flexible shaft 86, which rotates the rotating body 85 about a horizontal axis.

The flexible shaft 86, by rotating it about the axis thereof with a motor or knob (not shown in the drawing) provided at the control apparatus 14, transmits the rotary force thereof to the rotating body 84 and then to the cam 83.

Reference numeral 87 in the drawing is a distance sensor for detecting the position of the lens barrel 81*b*.

With the scanning microscope examination apparatus 80 according to this embodiment, having such a configuration, like the first and second embodiments, it is possible to move the focal position without moving the end surface of the objective lens unit 21, but keeping it abutting against the subject A.

It is possible to rotate the cam 83 directly using a motor instead of with the flexible shaft 86 and rotating body 85.

Next, a scanning microscope examination apparatus 90 according to a fourth embodiment of the present invention will be described below with reference to FIG. 13.

Figure 13:
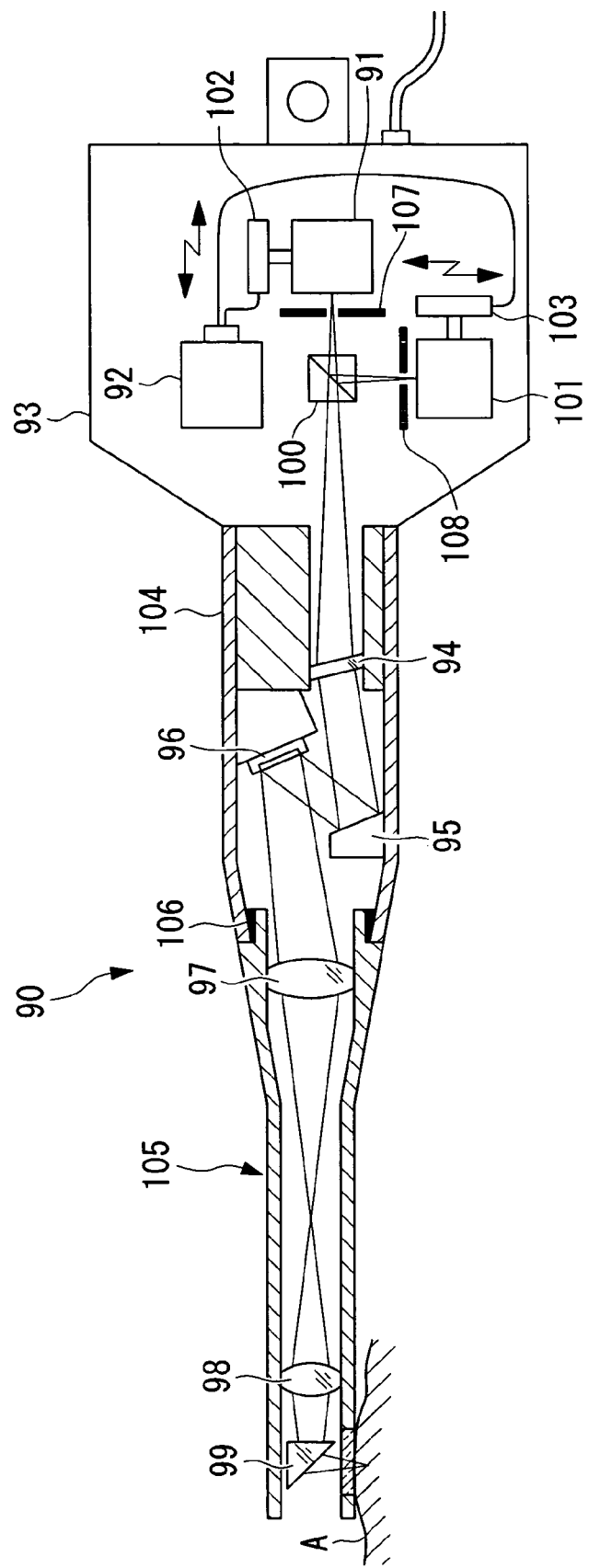
FIG. 13 is a longitudinal sectional diagram showing the detailed configuration of a scanning microscope examination apparatus according to a fourth embodiment of the present invention.

As shown in FIG. 13, the scanning microscope examination apparatus 90 according to this embodiment is an example in which a light source 91 and a control apparatus 92 are disposed inside a microscope examination apparatus main body 93.

The scanning microscope examination apparatus 90 according to this embodiment includes a light source 91; a collimator 94 for converting the light emitted from the light source 91 into a collimated beam; a fixed mirror 95 for reflecting the collimated beam emitted from the collimator 94; a galvanometer mirror unit 96 for two-dimensionally scanning the light reflected by the fixed mirror 95; a pupil-projection lens 97; an objective lens 98; a deflecting mechanism 99 for deflecting the light transmitted through the objective lens 98 by 90° and irradiating the subject A; a beam-splitter 100 for splitting off fluorescence returning from the subject A via the deflecting mechanism 99, the objective lens 98, the pupil-projection lens 97, the galvanometer mirror unit 96, the fixed mirror 95, and the collimator 94; and a light detector 101 for detecting the split off fluorescence.

The light source 91 and the light detector 101 are provided with linear-motion mechanisms 102 and 103 for respectively moving the light source 91 and the light detector 101 in the optical-axis directions. The linear-motion mechanisms 102 and 103 are controlled by the control apparatus 92. The control apparatus 92 operates the linear-motion mechanisms 102 and 103 based on image information input by an inputting unit 58; at this time, the system is configured so that the linear-motion mechanism 102 of the light source 91 and the linear-motion mechanism 103 of the light detector 101 are moved by the same distances along their respective optical axes.

The collimator 94, the fixed mirror 95, and the galvanometer mirror unit 96 are disposed inside a cylindrical chassis 104 fixed to the microscope examination apparatus main body 93, and a cylindrical lens unit 105 which includes the pupil-projection lens 97, the objective lens 98, and the deflecting mechanism 99 is fixed to the chassis 104 using a watertight seal 106.

Reference numerals 107 and 108 in the drawing are pinholes for stopping down the light emitted from the light source 91.

With the scanning microscope examination apparatus 90 according to this embodiment, having such a configuration, by moving the light source 91 along the optical axis, like the scanning microscope examination apparatuses 1, 70, and 80 of the first to third embodiments, it is possible to move the focal position without changing the position of the tip of the lens unit 105, and it is therefore possible to adjust the focal position while keeping the tip position of the lens unit 105 pressed against the subject A. Furthermore, because the light guided from the lateral direction is deflected by the deflecting mechanism 99 and irradiates the subject A, an advantage is provided in that the field of view of the stereomicroscope examination apparatus 4 is not blocked further.

As shown in FIG. 3, image information about the image to be acquired, for example, the magnification of the image, the depth position of the image, the field of view of the image, or the frame rate, is input by the inputting unit 58. Instead of this, however, as shown by the broken line in FIG. 3, it is also acceptable to provide a position detector for detecting the position of the actuator; to calculate, using the control apparatus 57, the image information of the image to be acquired by the light detector 13 based on the detected position of the actuator; and to display it on an image-information display device after correcting it based on information about the inherent errors of the objective lens unit 21 and the optical system inside the chassis 20.

In this case, the position detection of the actuator is done by the rotation angle detector of the stepping motor 35 in the first embodiment and a position detector such as an encoder (not shown); the encoder 75 in the second embodiment; the distance sensor 88 in the third embodiment; and encoders (not shown) attached to the linear-motion mechanisms 102 and 103 in the fourth embodiment.

In this case, the position detection of the actuator is done by the rotation-angle detector of the stepping motor 35 in the first embodiment or a position detector such as an encoder (not shown); the encoder 75 in the second embodiment; the distance sensor 88 in the third embodiment; and encoders (not shown) attached to the linear-motion mechanisms 102 and 103 in the fourth embodiment.

Additional Items

The invention with the following configurations is derived from these embodiments.

1. An optical-scanning microscope apparatus comprising a light source; a light-transmitting member for transmitting light from the light source; a collimator optical system for making the light transmitted by the light-transmitting member a collimated beam; a beam-scanning unit for scanning the collimated beam issuing from the collimator optical system at a subject; a focusing optical system for focusing the beam scanned by the beam-scanning unit onto the subject; a pupil-projection optical system disposed between the focusing optical system and the beam-scanning unit; a light detector for detecting return light returning from the subject via the focusing optical system, the pupil-projection optical system, the beam-scanning unit, the collimator optical system, and the light-transmitting member; an actuator for moving an end portion of the light-transmitting member, the collimator optical system, or the pupil-projection optical system in an optical-axis direction; a control apparatus for controlling driving of the actuator; and a deflecting mechanism for deflecting the light issuing from the light-transmitting member in a direction orthogonal to an optical axis thereof, wherein the actuator is disposed in a space parallel to a plane including optical axes before and after deflection by the deflecting mechanism.

According to this invention, the light emitted from the light source is transmitted through the light-transmitting member and is converted to a collimated beam by the collimator optical system. The collimated beam from the collimator optical system is scanned by the beam-scanning unit and is irradiated onto the subject via the pupil-projection optical system and the focusing optical system. The return light from the subject returns along the same optical path via the focusing optical system, the pupil-projection optical system, the beam-scanning unit, the collimator optical system, and the light-transmitting member and is detected by the light detector.

The light issuing from the light-transmitting member is deflected in an intersecting direction by the deflecting mechanism. Therefore, it is possible to guide the light towards the subject from a lateral direction with respect to the optical-axis direction of the focusing optical system. As a result, the height dimension, from the subject, of the optical system from the collimator optical system to the focusing optical system can be reduced, and there is thus no interference with the stereomicroscope which is disposed thereabove.

Because the actuator for moving any one of the tip portion of the light-transmitting member, the collimator optical system, and the pupil projection optical system is disposed in a space parallel to a plane including the optical axes before and after deflection by the deflecting mechanism, the actuator does not protrude in the lateral direction, it is possible to reduce the projection area on the subject, and it thus does not interfere with the stereomicroscope.

By operating the actuator to move one of the end portion of the light-transmitting member, the collimator optical system, and the pupil projection optical system in the optical-axis direction, by operating the control apparatus, it is possible to change the focal position while keeping the position of the tip of the focusing optical system fixed. In other words, it is possible to carry out observation while keeping the tip of the focusing optical system pressed against the subject, such as a small laboratory animal. As a result, image blurring due to pulsing of the subject can be prevented, which allows clear images to be acquired.

2. An optical-scanning microscope apparatus according to Additional Item 1, wherein a connecting portion for the actuator and the end portion of the light-transmitting member, the collimator optical system, or the pupil projection optical system moved by the actuator is connected via a spherical bearing in such a manner as to be capable of rotating about an axis orthogonal to the optical axes before and after deflection by the deflecting mechanism.

According to this invention, when the end portion of the light-transmitting member, the collimator optical system, or the pupil projection optical system is moved by operating the actuator, a force is applied from the actuator to the connecting portion. If the end portion of the light-transmitting member, the collimator optical system, or the pupil-projection optical system are reduced in size, a wrenching force due to the frictional force with the surroundings acts when displacement occurs; however, by causing the connecting portion to rotate about the axis orthogonal to the optical axes before and after deflection by the deflecting mechanism to loosen that force, it is possible to achieve smooth motion.

Using the spherical bearing, it is possible to achieve the above effect with a simple configuration.

3. An optical-scanning microscope apparatus according to Additional Item 1 or Additional Item 2, wherein the actuator includes a lead screw, a driving mechanism for rotationally driving the lead screw about an axis thereof; and a nut which engages with the lead screw and which has the connecting portion.

By operating the driving mechanism, the lead screw is rotated about the axis thereof, and the nut which is engaged with the lead screw is moved in a straight line along the longitudinal direction of the lead screw. Because the connecting portion is provided on the nut, by moving the nut in a straight line, it is possible to easily move one of the end portion of the light-transmitting member, the collimator optical system, and the pupil projection optical system, which allows the focal position to be adjusted.

4. An optical-scanning microscope apparatus according to Additional Item 1 or Additional Item 2, wherein the actuator is formed of a plunger which moves a shaft, at the end of which the connecting portion is connected, in the longitudinal direction thereof.

5. An optical-scanning microscope apparatus according to Additional Item 1 or Additional Item 2, wherein the actuator includes a cam having a cam surface which moves in the optical-axis direction, and a cam follower which is connected to one of the end portion of the light-transmitting member, the collimator optical system, and the pupil-projection optical system moved by the actuator and which is moved in the optical axis direction by the cam.

Similarly, this enables a simple actuator configuration.

6. An optical-scanning microscope apparatus according to Additional Item 5, further comprising an angle detector for detecting a rotation angle of the cam.

By detecting the rotation angle of the cam, it is possible to control the position of one of the end portion of the light-transmitting member, the collimator optical system, and the pupil projection optical system with good precision.

7. An optical-scanning microscope apparatus according to one of Additional Items 1 to 5, further comprising a movement-range detector for detecting both ends of the movement range of the end portion of the light-transmitting member, the collimator optical system, or the pupil-projection optical system moved by the actuator.

Because both ends of the movement range of the end portion of the light-transmitting member, the collimator optical system, or the pupil-projection optical system moved by the actuator are detected by the operation of the movement-range detector, they are prevented from moving outside the movement range.

8. An optical-scanning microscope apparatus according to one of Additional Items 1 to 7, wherein the beam-scanning unit is formed of a proximity galvanometer mirror.

According to the proximity galvanometer mirror, it is possible to simplify the construction of the beam-scanning unit, and in addition, the collimated beam from the collimator optical system can be scanned with high precision.

9. An optical-scanning microscope apparatus comprising a light source; a beam-scanning unit for scanning incident light from the light source on a subject; a focusing optical system for focusing the incident light scanned by the beam-scanning unit onto the subject; a deflecting mechanism for deflecting the light emitted from the light source in a direction intersecting an optical axis thereof; a splitting mechanism for splitting off from the incident light return light returning from the subject along the same optical path as the incident light, via the focusing optical system and the beam-scanning unit; a light detector for detecting the return light which is split off; a light-source moving mechanism for moving the light source in the optical-axis direction thereof; a detector moving mechanism for moving the light detector in the optical-axis direction thereof by an amount of movement equal to the amount of movement of the light source; and a control apparatus for controlling driving of the detector moving mechanism.

According to this invention, the light emitted from the light source is scanned by the beam-scanning unit and is irradiated onto the subject via the focusing optical system. Because the light from the light source is deflected in an intersecting direction by the deflecting mechanism and is irradiated onto the subject, it is possible to make the light incident from a lateral direction with respect to the irradiation direction of the subject, and therefore it is possible to ensure that observation by the stereomicroscope etc. is not obstructed. The return light from the subject returns along the same path via the focusing optical system and the beam-scanning unit, is split off from the incident light by the splitting mechanism, and is detected by the light detector. In this case, changing the position of the light source by operating the light-source moving unit allows the focal position to be adjusted without changing the position of the end of the focusing optical system. In addition, moving the detector by the same amount of movement as the amount of movement of the light source, by operating the control mechanism, allows a clear image to be acquired.

To perform in-vivo examination of various organs of a small laboratory animal, such as a rat or mouse, using the optical-scanning microscope apparatus, it is necessary to reduce the diameter of the objective lens unit of the microscope apparatus to allow the objective lens unit of the microscope apparatus to be brought close to the small laboratory animal, which is the subject. If the focusing optical system is reduced in diameter, the objective lens and a mechanical part for holding it become small, and errors in magnification and focal position occur in the assembly process. The errors inherent to each objective lens unit must be corrected when mounting the objective lens unit to the microscope main body. With the optical-scanning microscope apparatuses in the related art, it is not assumed that errors occurring due to individual differences in the objective lenses and mechanical parts holding them are corrected.

Additional Items 34 to 55 below are conceived in light of the circumstances described above, and an object thereof is to correct errors inherent to the objective lens unit when mounting the objective lens unit to the microscope main body.

10. An optical-scanning microscope apparatus comprising a light source; a light-transmitting member for transmitting light from the light source; a collimator optical system for converting the light transmitted by the light-transmitting member into a collimated beam; a beam-scanning unit for scanning the collimated beam issuing from the collimator optical system on a subject; a focusing optical system for focusing the light scanned by the beam-scanning unit onto the subject; a pupil-projection optical system disposed between the focusing optical system and the beam-scanning unit; a light detector for detecting return light returning from the subject via the focusing optical system, the pupil-projection optical system, the beam-scanning unit, the collimator optical system, and the light-transmitting member; an actuator for moving an end portion of the light-transmitting member, the collimator optical system, or the pupil-projection optical system in an optical-axis direction; and a control apparatus for controlling driving of the actuator, wherein the end portion of the light-transmitting member, the collimator optical system, the beam-scanning unit, and the pupil-projection optical system are contained in a chassis, and the focusing optical system is connected to the chassis in such a manner as to be capable of being attached and detached.

11. An optical-scanning microscope apparatus according to Additional Item 10, wherein a code indicating information inherent to the focusing optical system is provided in the focusing optical system, a reading apparatus for reading the code is provided in the chassis, and the control apparatus controls the actuator based on the read code.

According to this invention, even if there are errors inherent to each focusing optical system, they can be corrected when mounting the focusing optical system, and it is thus possible to display desired image settings and image information during acquisition.

12. An optical-scanning microscope apparatus according to Additional Item 11, further comprising a database for associating and storing the code and the information inherent to the focusing optical system, wherein the control apparatus searches the database using the code read by the reading apparatus as a key and controls the actuator based on the obtained information inherent to the focusing optical system.

By doing so, it is possible to store the information inherent to the focusing optical system in the database and to simplify the code. In addition, it is possible to obtain many types of information about lens data, aberrations, and so on using the simple code, and it is possible to control the actuator with good precision.

13. An optical-scanning microscope examination apparatus according to Additional Item 12, further comprising an image correcting mechanism which associates and stores the code and aberration information about the focusing optical system in the database, which searches the database using the code read by the reading apparatus as a key, and which corrects the image of the subject detected by the light detector based on the obtained aberration information about the focusing optical system.

According to this invention, because the aberration information about the focusing optical system is obtained from the database using the code read by the reading apparatus as a key, it is possible to obtain a clear image by correcting the image with the image correcting mechanism based on the obtained aberration information.

14. An optical-scanning microscope apparatus according to one of Additional Items 10 to 13, wherein the focusing optical system and the chassis are connected in a watertight manner.

By connecting both of them in a watertight manner, it is possible to prevent liquid from getting in between the focusing optical system and the chassis even in an environment where liquid or cleaning liquid is present, such as when observing inside the body of a small laboratory animal, for example.

15. An optical-scanning microscope apparatus according to one of Additional Items 10 to 14, further comprising a contact sensor for detecting contact of the focusing optical system with the chassis.

Because contact of the focusing optical system with the chassis is detected by operating the contact sensor, it is possible to prevent pointless operations or entry of liquid due to performing examination with faulty mounting.

16. An optical-scanning microscope apparatus according to one of Additional Items 10 to 15, wherein the chassis is connected to the control apparatus via the connector in such a manner as to be capable of being attached and removed; an in-chassis-optical-system code indicating information inherent to the collimator optical and the pupil-projection optical system inside the chassis is provided in the chassis; an in-chassis-optical-system information reading apparatus for reading the in-chassis-optical-system code is provided in the connector; and the control apparatus controls the actuator based on the read in-chassis-optical-system code.

When the chassis and the control apparatus are connected via the connector, the in-chassis-optical-system code provided on the chassis is read by the in-chassis-optical-system information reading apparatus provided in the connector. Because there is an optical system having inherent information in the chassis, such as the collimator optical system and the pupil projection optical system, by reading it and controlling the actuator based on the read in-chassis-optical-system code, it is possible to perform focal position adjustment more precisely.

17. An optical-scanning microscope apparatus according to Additional Item 16, further comprising a second database for associating and storing the in-chassis-optical-system code and the information inherent to the collimator optical system and the pupil-projection optical system, wherein the control apparatus searches the second database using the in-chassis-optical-system code read by the in-chassis-optical system information reading apparatus as a key, and controls the actuator based on the information obtained.

By doing so, the in-chassis-optical-system code can be simplified, and it is possible to obtain from the second database a lot of information about lens data, aberrations, and so forth, using the simple code, which allows actuator control to be carried out more precisely.

18. An optical-scanning microscope examination apparatus according to one of Additional Items 10 to 17, wherein the in-chassis-optical-system code and aberration information about the collimator optical system and the pupil-projection optical system are associated and stored in the second database; the image correction mechanism searches the second database using as a key the in-chassis-optical-system code read by the in-chassis-optical-system reading apparatus and corrects the image of the subject detected by the light detector based on the obtained aberration information about the collimator optical system and the pupil-projection optical system.

According to this invention, because the aberration information about the collimator optical system and the pupil-projection optical system is obtained from the second database using as a key the in-chassis-optical-system code read by the in-chassis-optical-system information reading apparatus, it is possible to obtain a clear image by correcting the image with the image correcting mechanism based on the obtained aberration information.

19. An optical-scanning microscope examination apparatus according to Additional Item 10 further comprising a position detector for detecting the position of an end portion of the light-transmitting member, the collimator optical system, or the pupil projection optical system, which are moved by the actuator.

By detecting the position of the end portion of the light-transmitting member, the collimator optical system, or the pupil-projection optical system using the position detector, it is possible to achieve more precise control.

20. An optical-scanning microscope examination apparatus according to Additional Item 19, further comprising an inherent-information inputting unit for inputting inherent information about the focusing optical system, and further comprising an image-information calculating unit for calculating image information about the image to be acquired by the light detector based on the position of the end portion of the light-transmitting member, the collimator optical system, or the pupil-projection optical system moved by the actuator, which position is detected by the position detecting unit, and the input inherent information of the focusing optical system, and an image-information display unit for displaying the calculated image information.

In this way, because the image-information calculating unit calculates the image information of the image to be acquired, based on the position of the end portion of the light-transmitting member, the collimator optical system, or the pupil-projection optical system and the inherent information of the focusing optical system, more-precise image information is displayed on the image-information display unit.

21. An optical-scanning microscope examination apparatus according to Additional Item 20, wherein the inherent information in the focusing optical system is any one of the magnification of the focusing optical system, the depth, or the field of view.

By inputting the inherent magnification in the focusing optical system, regardless of variations in any one of the magnification, the depth, or the field of view due to individual differences, it is possible to display more-precise image information.

22. An optical-scanning microscope examination apparatus according to Additional Item 19, further comprising an optical-system-information inputting unit for inputting information inherent to the collimator optical system and the pupil-projection optical system; and further comprising an image-information calculating unit for calculating image information of an image to be acquired by the light detector based on the position of the end portion of the light-transmitting member, the collimator optical system, or the pupil-projection optical system moved by the actuator, which position is detected by the position detecting unit, and the input information inherent to the collimator optical system and the pupil-projection optical system; and an image-information display unit for displaying the calculated image information.

Because the image-information calculating unit calculates the image information of the image to be acquired by the light detector using the information inherent to the collimator optical system and the pupil-projection optical system input by the optical-system-information inputting unit, it is possible to display higher precision image information, regardless of individual differences in the collimator optical system and the pupil-projection optical system.

23. An optical-scanning microscope examination apparatus according to Additional Item 22, wherein the information inherent to the collimator optical system and the pupil-projection optical system is the magnification of the collimator optical system and the pupil-projection optical system.

In particular, when the size is reduced and sufficient processing precision cannot be obtained, the magnifications of the collimator optical system and the pupil-projection optical system exhibit individual differences; however, because information about the magnification, even though it varies, is input with the optical-system-information inputting unit, it is possible to calculate high-precision image information based on this, which can be displayed on the image-information display unit.

24. An optical-scanning microscope apparatus according to Additional Item 10, further comprising an image-information inputting unit for inputting image information about an image to be acquired by the light detector, wherein the control apparatus controls the actuator based on the image information input with the image-information inputting unit, and the image information is any one of the magnification, depth, or field of view of the image to be acquired.

By displaying this information using the image-information display unit, the user can improve current image-capturing conditions and the observation precision of the image acquired.

25. A storage container for accommodating a focusing optical system of a laser scanning microscope including a beam-scanning unit having an optical fiber, a collimator mechanism, and a beam-scanning mechanism; and the focusing optical system which has a long, thin, rigid, cylindrical inserting portion and which is attached to the beam-scanning unit in such a manner as to be capable of being attached and removed, the storage container comprising a code for indicating inherent information of the focusing optical system.

According to this invention, even in cases where it is not possible to attach a code because the focusing optical system is too small, it is possible to use the code of the focusing optical system, and in addition, it is possible to input the code even when the focusing optical system is already attached to a living organism.

26. A storage container according to Additional Item 25, wherein the code is a radio-frequency identification device (RFID).

With this configuration, it is possible to read the code easily.

27. A storage container according to Additional Item 25 or Additional Item 26, wherein the code includes at least one type of information from magnification, numerical aperture, corresponding wavelength region, or observation atmosphere.

By reading the code, it is possible to easily acquire these types of information.

An optical-scanning microscope examination apparatus 201 according to a fifth embodiment of the present invention will be described with reference to FIG. 15 and FIG. 16.

Figure 15:
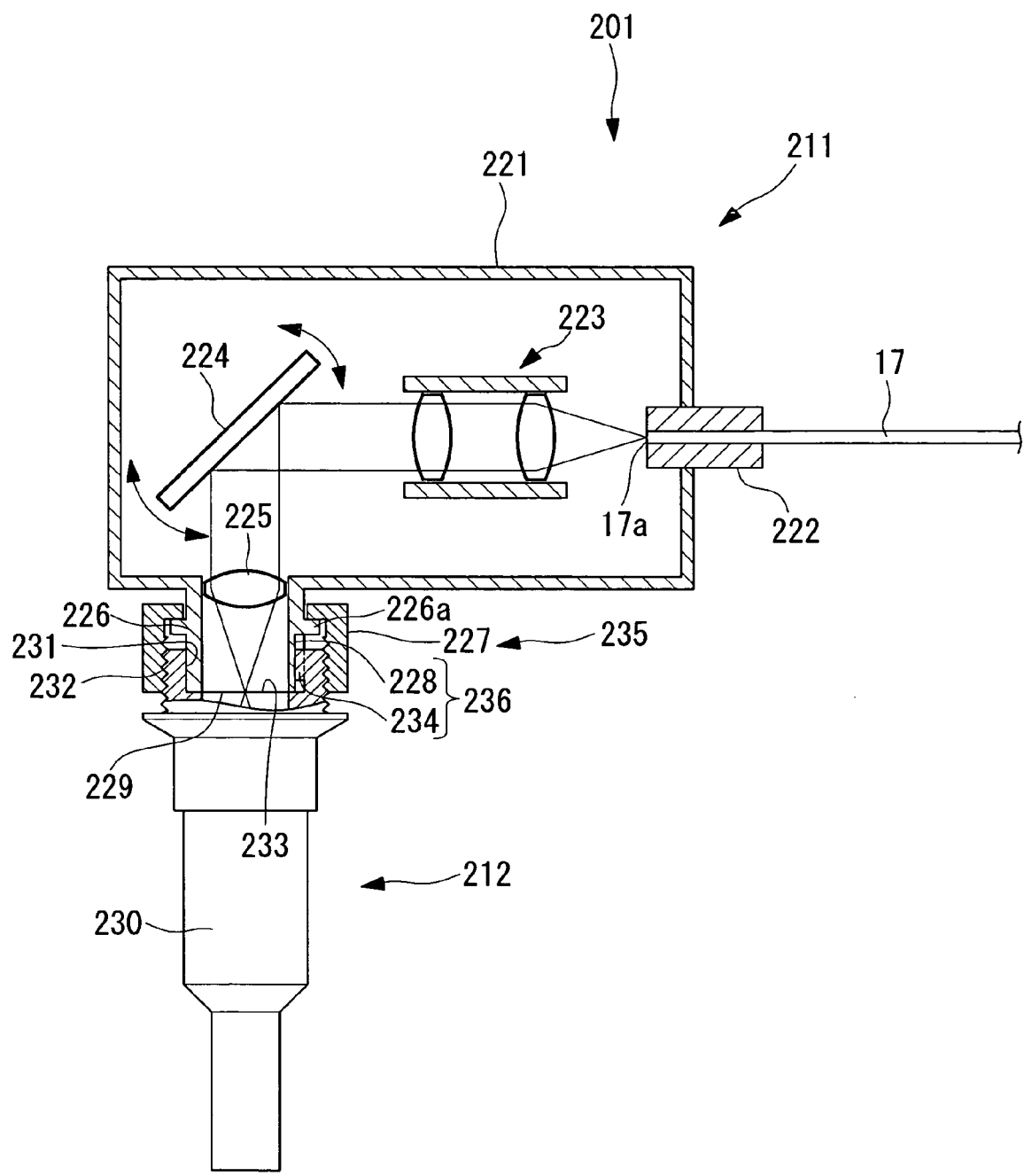
FIG. 15 is a diagram showing the internal configuration of an optical-scanning microscope examination apparatus according to a fifth embodiment.

As shown in FIG. 15, the optical-scanning microscope examination apparatus 201 according to this embodiment includes a microscope examination apparatus main body (apparatus main body) 211 and an objective lens unit (objective unit) 212 which is coupled to the microscope examination apparatus main body 211; in this embodiment, for example, a laser light source is used as a light source 12, and, for example, a photomultiplier tube (PMT) is used as a light detector 13.

As shown in FIG. 15, the microscope examination apparatus main body 211 includes, in a chassis 211 that is attached at one end of an optical fiber 17, a ferrule 222 for securing the end of the optical fiber 17, a collimator optical system 223 for converting the light issuing from an end face 17a of the optical fiber 17 into a collimated beam, a beam-scanning unit 224 for two-dimensionally scanning the light issuing from the collimator optical system 223, and a pupil-projection optical system 225 for collecting the light scanned by the beam-scanning unit 224 and forming an intermediate image.

A nut 227, which is attached in such a manner as to be incapable of falling off by a stopper 226a formed on the outer circumferential surface of a cylindrical tube 226 for accommodating the pupil-projection optical system 225 and which is held so as to be freely rotatable about the center axis of the cylindrical tube 226, is provided in the microscope examination apparatus main body 211. A key groove 228 is formed along the longitudinal direction in the outer circumferential surface of the cylindrical tube 226. An end surface of the cylindrical tube 226 serves as an abutting surface 229 against which the objective lens unit 212 (described later) abuts when coupled. The position of the intermediate image formed by the pupil-projection optical system 225 is substantially coincident with the position of the abutting surface 229.

On the other hand, the objective lens unit 212 accommodates an objective lens (not shown in the drawing) inside an outer tube 230, and at one end of the outer tube 230, there is a mating hole 231 for mating with the cylindrical tube 226 and a threaded portion 232 to which the nut 227 is fastened. In a toothed portion of the mating hole 231, by fastening the nut 227 onto the threaded portion 232, an abutting surface 233 which abuts the abutting surface 229 at the end of the cylindrical tube 226 is provided.

An attaching-and-detaching mechanism 235 for attaching the objective lens unit 212 to the microscope examination apparatus main body 11 in such a manner that it is capable of being attached and removed is formed by the nut 227, the key groove 228, the threaded portion 232 of the objective lens unit 212, and key member 234. A rotation lock 236 for preventing the objective lens unit 212 from rotating relative to the microscope examination apparatus main body 211 is formed by the key groove 228 and the key member 234.

The operation of the optical-scanning microscope examination apparatus 201 according to this embodiment, having such a configuration, will be described below.

To observe the subject A with the examination system 2 described above, first, the subject A, which is a small laboratory animal or the like, including a mouse or rat, is fixed to the stage 3, and while displaying an image of the examination site on the first monitor 10 using the stereomicroscope apparatus 4 disposed thereabove, the skin is incised to expose an internal organ. At this time, the microscope examination apparatus main body 211 of the optical-scanning microscope examination apparatus 201 is located at a position away from the field of view of the stereomicroscope apparatus 4.

In the optical-scanning microscope examination apparatus 201, the objective lens unit 212 which is used to achieve the desired observation magnification is attached to the microscope examination apparatus main body 212. The objective lens unit 212 and the microscope examination apparatus main body 211 are sealed with an O-ring or the like (not shown in the drawing) so that moisture cannot get inside.

Once preparations have been completed, the microscope examination apparatus main body 211 of the optical-scanning microscope examination apparatus 201 is inserted between the stereomicroscope apparatus 4 and the subject A.

The laser light emitted from the light source 12 passes through the dichroic mirror 56, is introduced into the optical fiber 17, propagates through the optical fiber 17, and emerges from the end face 17a, which is secured by the ferrule 222, into the chassis 221 of the microscope examination apparatus main body 211. Inside the microscope examination apparatus main body 211, the laser light issuing from the end face 17a of the optical fiber is converted to a collimated beam by the collimator optical system 223, and after being two-dimensionally scanned by the beam-scanning unit 224, an intermediate image is formed by the pupil-projection optical system 225, and is introduced into the objective lens unit 212. The laser light transmitted through the objective lens unit 212 forms a focal point at the subject A and excites a fluorescent material or an autofluorescent material, which is injected into the subject A in advance, to generate fluorescence.

The fluorescence generated in the subject A returns along the same path as the laser light, via the objective lens unit 212, the pupil-projection optical system 225, the beam-scanning unit 224, the collimator optical system 223, and the optical fiber 17, is split off by the dichroic mirror 56, and is detected by the light detector 13. In this case, because the position of the end face 17a of the optical fiber secured to the microscope examination apparatus main body 211, the position of the intermediate image formed by the pupil projection optical system 225, and the position of the focus formed by the objective lens unit 212 are disposed in a conjugate positional relationship to each other, the end face 17a of the optical fiber 17 functions as a confocal pinhole, and therefore, only fluorescence from close to the focal position in the subject A is detected in the light detector 13.

With the optical-scanning microscope examination apparatus 201 according to this embodiment, after specifying the examination site on the subject A once at observation time, when re-observing the same examination site over time, by loosening the nut 227 of the attaching-and-detaching mechanism 235, it is possible to separate the microscope examination apparatus main body 211 from the objective lens unit 212, and the objective lens unit 212 can remain attached to the subject A. In other words, at times other than during observation, only the objective lens unit 212, which is comparatively light, is attached to the subject A, rather than attaching the microscope examination apparatus main body 211, which is relative heavy. Therefore, the burden placed on the subject A is reduced.

When separating the objective lens unit 212 from the microscope examination apparatus main body 211, the nut 227 is attached in such a manner as to be freely rotatable relative to the microscope examination apparatus main body 211, and due to the action of the rotation stop 236, the objective lens unit 122 does not rotate relative to the microscope examination apparatus main body 211. Therefore, it is possible to separate the microscope examination apparatus main body 211 without rotating the objective lens unit 212, which is located at the examination site, relative to the subject A.

When attaching the microscope examination apparatus main body 211 to the objective lens unit 212 remaining at the subject A, the cylindrical tube 226 is mated with the mating hole 231 with the phase of the microscope examination apparatus main body 211 matched with the objective lens unit 212 so that the key member 234 of the objective lens unit 212 is aligned with the key groove 228 in the microscope examination apparatus main body 211. By rotating the nut 227, the microscope examination apparatus main body 211 is moved, by means of the threaded portion 232 which is engaged with the nut 227, in such a direction that it approaches the objective lens unit 212. Because the key member 234 is inserted in the key groove 228, so long as the microscope examination apparatus main body 211 does not rotate, it is possible to join the microscope examination apparatus main body 211 and the objective lens unit 212 without the objective lens unit 212 rotating relative to the subject A.

As a result, when separating the microscope examination apparatus main body 211 from the objective lens unit 212 and keeping it at the subject A, and when connecting the microscope examination apparatus main body 211 to the objective lens unit 212 which is kept at the subject A, the objective lens unit 212 is prevented from shifting relative to the examination site, and it is thus possible to observe the same examination site in multiple examinations at intervals of time. In addition, because it is possible to prevent shifting of the objective lens unit 212 relative to the examination site, the burden placed on the subject A is reduced, and the subject A thus remains healthy over an extended period of time. In other words, it is possible to carry out in-vivo examination of the subject A, which is a small laboratory animal or the like such as a mouse, for an extended period of time.

In the optical-scanning microscope examination apparatus 201 according to this embodiment, when the objective lens unit 212 is connected to the microscope examination apparatus main body 211, the abutting surface 229 provided at the end of the cylindrical tube 226 of the microscope examination apparatus main body 211 and the abutting surface 233 provided at the toothed portion of the mating hole 231 in the objective lens unit 212 are connected so as to abut against each other. In other words, these abutting surfaces 229 and 233 constitute a shoulder position for locating the pupil-projection optical system 225 and the objective lens unit 212 in the optical-axis direction. Because the position of the intermediate image formed by the pupil-projection optical system 225 is provided so as to be substantially coincident with the position of the abutting surface 229, it is possible to minimize errors in position, orientation, etc. which occur when connecting the objective lens unit 212 to the microscope examination apparatus main body 211.

In the optical-scanning microscope examination apparatus 201 according to this embodiment, because the nut 227 constituting the attaching-and-detaching mechanism 235 is provided in the microscope examination apparatus main body 211 in such a manner as to be freely rotatable, compared to a case where the nut 227 is provided in each objective lens unit 212, when there is a plurality of objective lens units 212, an advantage is afforded in that it is possible to reduce the number of parts. Also, except for the problem of parts count, the nut 227 constituting the attaching-and-detaching mechanism 235 may be provided in each objective lens unit 212 in such a manner as to be freely rotatable. Although the attaching-and-detaching mechanism 235 has been illustrated by an example in which connection is achieved by fastening the nut 227 and the threaded portion 232, instead of this, it is also possible to employ another type of known attaching-and-detaching mechanism, such as a bayonet type or the like.

In the optical-scanning microscope examination apparatus 201 according to this embodiment, it is considered difficult to see the key groove 228 provided in the cylindrical tube 226 from outside because it is covered by the nut 227. Therefore, as shown in FIG. 16, on the cylindrical tube 226 of the microscope examination apparatus main body 211, it is preferable to provide a mark 238 indicating the position of the key groove 228 at a position which can be seen from outside, for example, on the side face of the chassis 221.

On the objective lens unit 212, it is preferable to provide a mark 239, indicating the position of the key member 234, in the form of a straight line in the longitudinal direction from the tip of the objective lens unit 212. Accordingly, even if the tip of the objective lens unit 212 is disposed partially inserted inside the subject A, it is possible to easily confirm the phase of the key member 234 using the mark 239 provided on the exposed part outside the subject A.

If both of the marks 238 and 239 of the objective lens unit 212 and the microscope examination apparatus main body 211 are provided, there is no need at all to align and provide the marks 238 and 239 at the positions of the key member 234 in the objective lens unit 212 and the key groove 228 in the microscope examination apparatus main body 211. In other words, in this case, when the objective lens unit 212 is secured to the microscope examination apparatus main body 211, it is sufficient to provide each of the marks 238 and 239 in a mutually aligned phase relationship.

Figure 16:
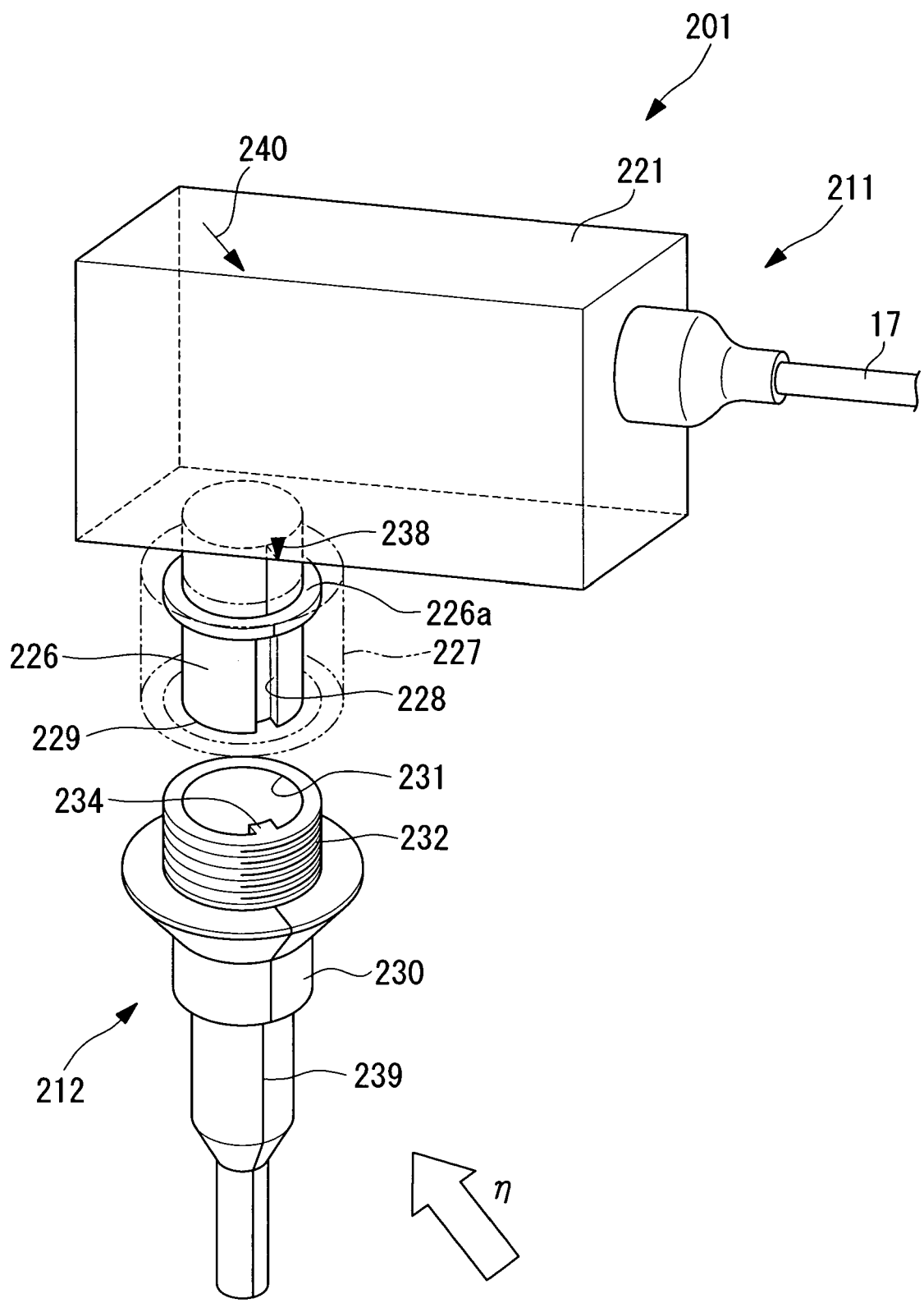
FIG. 16 is an exploded perspective view showing the optical-scanning microscope examination apparatus in FIG. 15.
Figure 17:
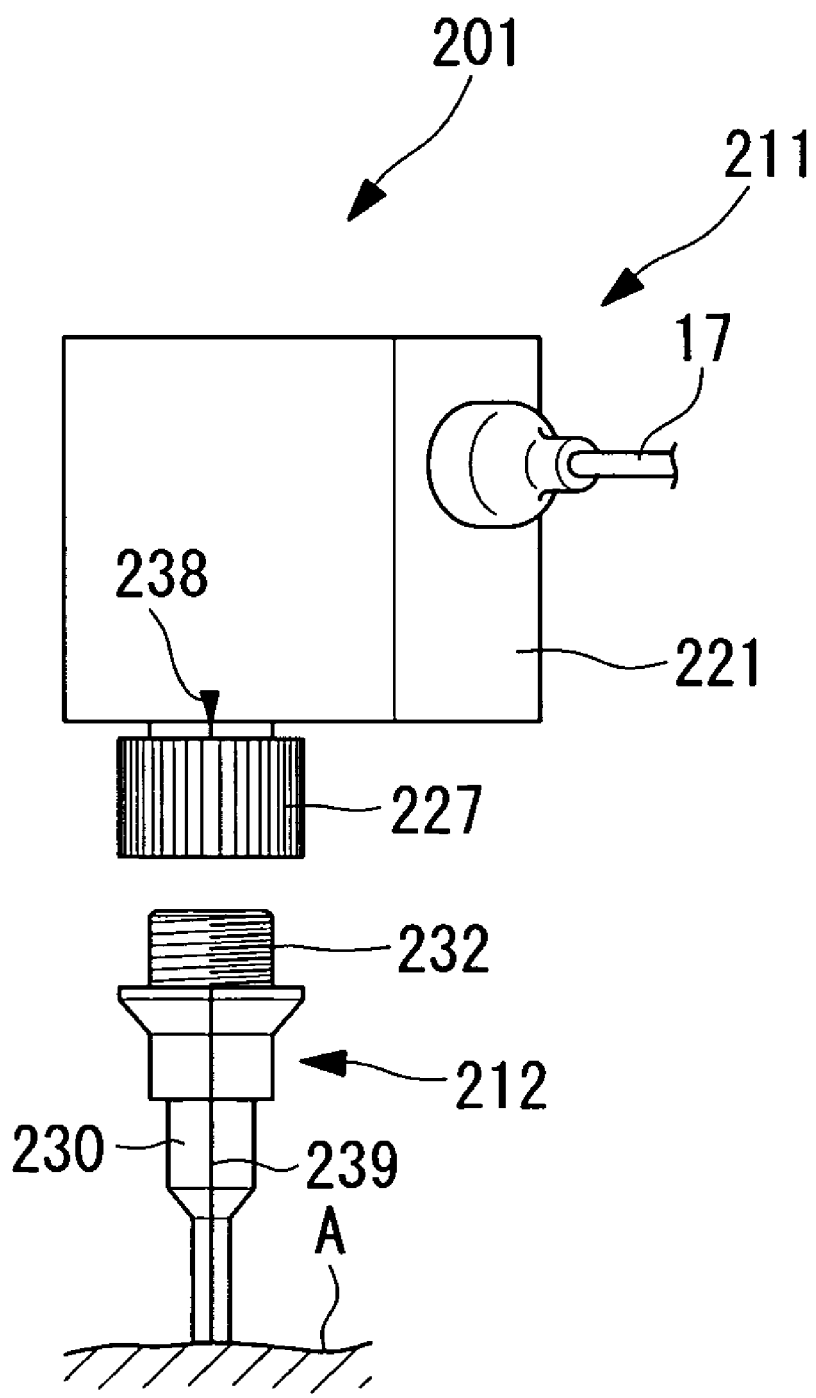
FIG. 17 is a diagram for explaining the sequence of operations for attaching an apparatus main body to an objective unit in the optical-scanning microscope examination apparatus in FIG. 15.

In this case, as shown in FIG. 17, viewing the objective lens unit 212 from the direction of arrow η shown in FIG. 16, when the mark 239 on the objective lens unit 212 is visible as a straight line, by positioning the microscope examination apparatus main body 211 in proximity so that the mark 238 on the microscope examination apparatus main body 211 is disposed on the extension of the mark 239, it is possible to connect the objective lens unit 212 and the microscope examination apparatus main body 211 without making the objective lens unit 212 rotate at all.

Figure 18A:
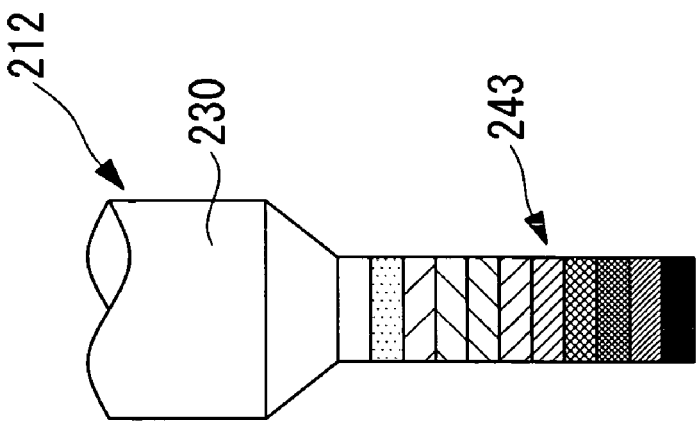
FIGS. 18 A to C are diagrams showing examples of marks displayed on the objective unit in the optical-scanning microscope examination apparatus in FIG. 15.
Figure 18B:
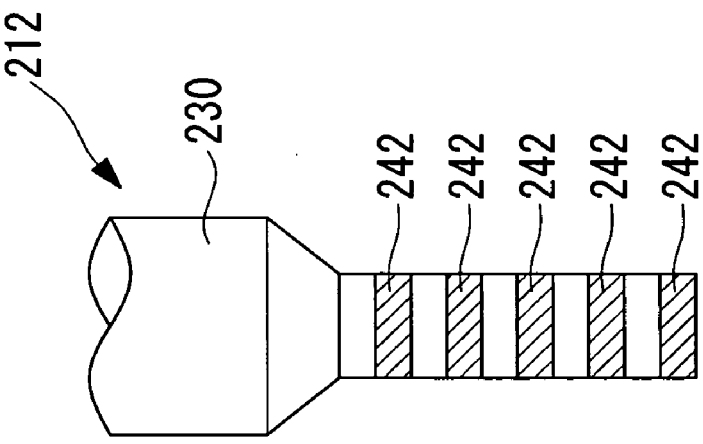
Figure 18C:
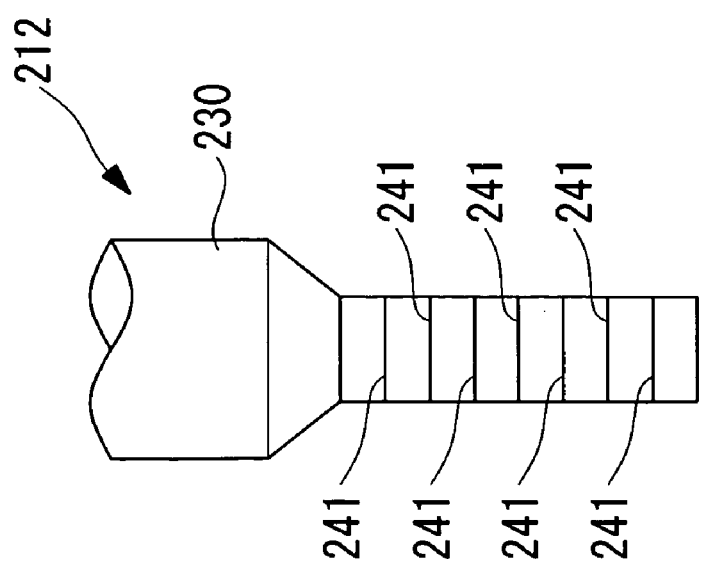

Marks 241 shown in FIG. 18A to FIG. 18C may be used as the mark provided on the outer circumferential surface of the objective lens unit 212.

In the marks 241 shown in FIG. 18A, a plurality of lines separated by equal gaps in the longitudinal direction are provided along the circumferential direction in the outer circumferential surface of an end portion of the objective lens unit 212. By setting the gaps of these marks 241 to a predetermined value, by counting the number of marks 241 exposed outside the subject A, it is possible to determine the insertion depth of the objective lens unit 212 in the subject A.

The marks 242 shown in FIG. 18 B, which are alternating gray regions, allow the insertion depth to be recognized in a similar manner as described above.

The marks 243 shown in FIG. 18 C are regions whose color density varies sequentially; for example, by processing an image G1 of the stereomicroscope apparatus 4, it is possible to determine the insertion depth from the color density of the exposed portion.

Figure 19:
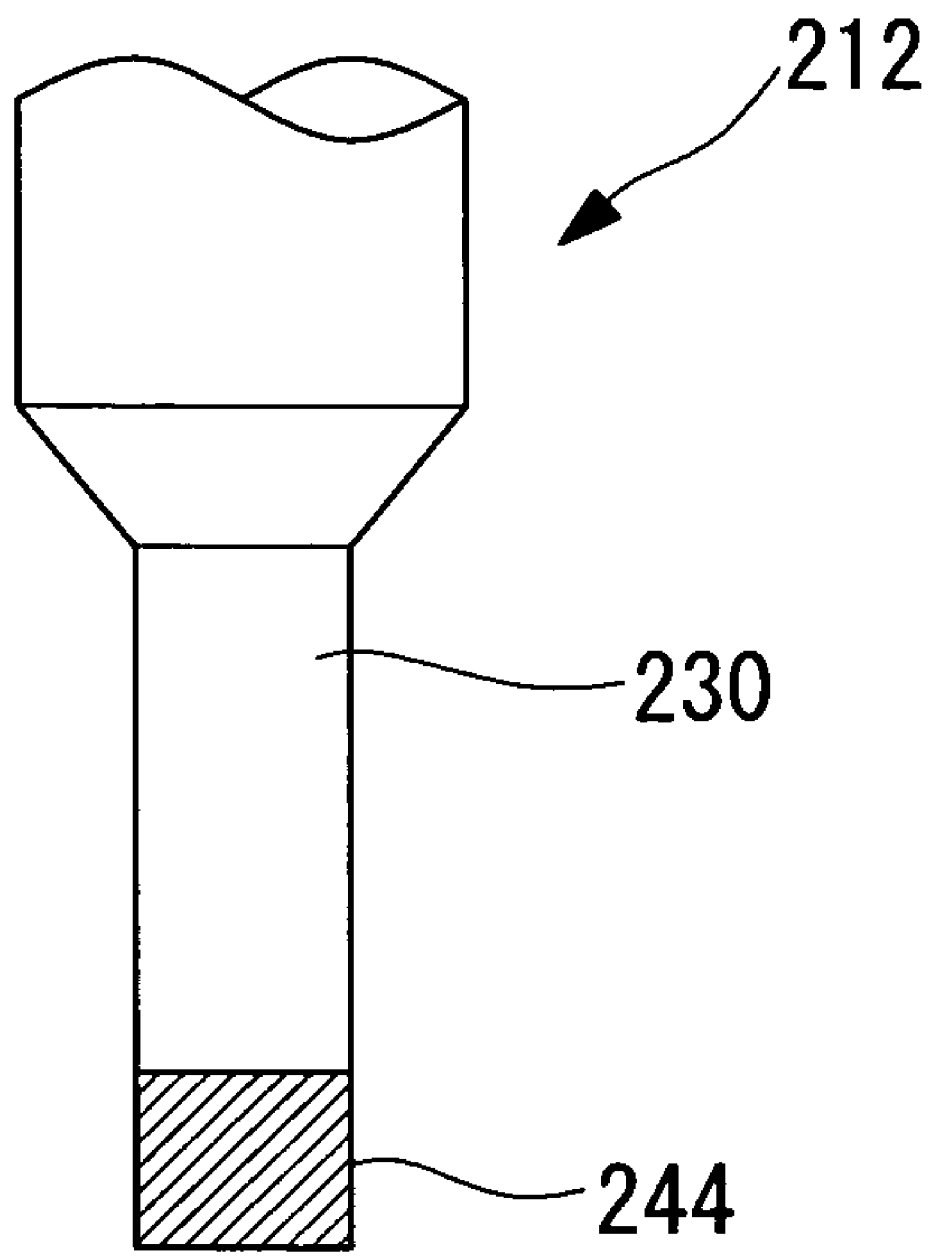
FIG. 19 is a diagram showing anti-reflection treatment applied to the objective unit in the optical-scanning microscope examination apparatus in FIG. 15.

In addition to the marks 241 to 243 described above, as shown in FIG. 19, it is preferable to apply anti-reflection treatment 244 to the end portion of the objective lens unit 212. By doing so, when observing with another examination apparatus, such as the stereomicroscope apparatus 4, it is possible to prevent light reflected by the outer surface of the objective lens unit 212 from interfering with the observation. The anti-reflection treatment may include black coating, matte processing, reflection-reduction coating, and so forth.

In the embodiment described above, the nut 227 and the threaded portion 232 constituting the attaching-and-detaching mechanism 235 may be formed with left-handed threads. With this construction, when rotating the nut 227 at the microscope examination apparatus main body 211 side with a hand approaching from the objective lens unit 212 side, because it is fastened by clockwise rotation and unfastened by anticlockwise rotation, an advantage is afforded in that the operator can perform the attaching and detaching procedure without any sense of unintuitiveness.

Additional Items

The invention with the following configurations is derived from these embodiments.

1. An optical-scanning microscope examination apparatus comprising a light source; an optical fiber for transmitting light from the light source; an apparatus main body accommodating a collimator optical system which converts the light transmitted by the optical fiber into a collimated beam and a beam-scanning mechanism for two-dimensionally scanning the collimated beam emitted from the collimator optical system; an objective unit which is attached to the apparatus main body in such a manner as to be capable of being attached and removed and which focuses the beam scanned by the beam-scanning mechanism onto an examination site; and a light detector for detecting return light returning via the objective unit, the apparatus main body, and the optical fiber, wherein the objective unit has an end portion which can be inserted inside the subject, and a mechanism for attaching and detaching the objective unit to and from the apparatus main body includes a rotation stop which stops relative rotation of the objective unit about a longitudinal axis relative to the apparatus main body during attachment and detachment.

2. An optical-scanning microscope examination apparatus according to Additional Item 1, wherein the attaching-and-detaching mechanism includes a first screw which is held on one of the apparatus main body and the objective unit in such a manner as to be freely rotatable about the longitudinal axis, and a second screw which is provided on the other one of the apparatus main body and the objective unit and which is engaged with the first screw.

By rotating the first screw about the longitudinal axis with the objective unit inserted in the longitudinal direction with respect to the apparatus main body and the first screw and the second screw engaged, the first screw and the second screw are fastened. At this time, because relative rotation of the objective unit and the apparatus main body is prevented by the rotation stop, both of them approach each other in the longitudinal-axis direction together as the first screw rotates. Because the first screw is held on one of the apparatus main body and the objective unit in such a manner as to be freely rotatable, it is possible to attach and detach the objective unit and the apparatus main body without relative rotation, using a simple configuration.

3. An optical-scanning microscope examination apparatus according to Additional Item 2, wherein the first screw is held on the apparatus main body.

By attaching the first screw to the apparatus main body in such a manner as to be freely rotatable, when using a plurality of objective units that can be exchanged, an advantage is provided in that it is possible to reduce the number of parts.

Other embodiments formed by partially combining the individual embodiments described above are also encompassed within the present invention.

The invention claimed is:

1. An optical-scanning microscope examination apparatus comprising:
   a light source that emits light;
   a light-transmitting member configured to transmit the light emitted by the light source;
   a collimator optical system for converting the light transmitted by the light-transmitting member into a collimated beam;
   a beam-scanning unit for scanning the collimated beam issuing from the collimator optical system on a subject;
   a focusing optical system for focusing the beam scanned by the beam-scanning unit on the subject;
   a pupil-projection optical system which is disposed between the focusing optical system and the beam-scanning unit;
   a light detector for detecting return light returning from the subject via the focusing optical system, the pupil-projection optical system, the beam-scanning unit, the collimator optical system, and the light-transmitting member;
   an actuator for moving an end portion of the light-transmitting member, the collimator optical system, or the pupil-projection optical system along an optical-axis direction of the light transmitted by the light-transmitting member;
   a control apparatus for controlling driving of the actuator; and
   a deflecting mechanism for deflecting the light issuing from the light-transmitting member in a direction intersecting the optical axis of the light transmitted by the light-transmitting member,
   wherein the actuator is disposed in a space formed on a plane parallel to optical axes before and after deflection by the deflecting mechanism.

2. An optical-scanning microscope examination apparatus according to claim 1, wherein a connecting portion of the actuator and the end portion of the light-transmitting member, the collimator optical system, or the pupil-projection optical system is connected in such a manner as to be capable of rotating about an axis orthogonal to the plane including the optical axes of the light transmitted by the light-transmitting member before and after deflection by the deflecting mechanism.

3. An optical-scanning microscope examination apparatus according to claim 1, wherein the deflecting mechanism is formed of the beam-scanning unit.

4. An optical-scanning microscope examination apparatus according to claim 1, further comprising a position detector for detecting the position of the end portion of the light-transmitting member, the collimator optical system, or the pupil-projection optical system.

5. An optical-scanning microscope examination apparatus according to claim 1, wherein the collimator optical system is provided so as to be capable of moving and includes a transparent member forming a seal between an end surface of the light-transmitting member and the collimator optical system.

6. An optical-scanning microscope examination apparatus according to claim 1, wherein the light emitting from the light source includes a plurality of wavelengths and the light source includes a selecting mechanism for selecting a wavelength of light emitted from the light source, and the control apparatus controls the actuator according to the wavelength selected by the selecting mechanism.

7. An optical-scanning microscope examination apparatus according to claim 1, wherein the end portion of the light-transmitting member, the collimator optical system, the beam-scanning unit, and the pupil-projection optical system are accommodated inside a chassis.

8. An optical-scanning microscope examination apparatus according to claim 7, wherein a window through which it is possible to observe part of the end portion of the light-transmitting member, the collimator optical system, or the pupil-projection optical system from outside is provided in the chassis.

9. An optical-scanning microscope examination apparatus according to claim 7, wherein the focusing optical system is attached to the chassis in such a manner as to be capable of being attached and removed.

10. An optical-scanning microscope examination apparatus according to claim 9, wherein a code indicating information inherent to the focusing optical system is provided in the focusing optical system, a reading apparatus for reading the code is provided in the chassis, and the control apparatus controls the actuator based on the code that is read.

11. An optical-scanning microscope examination apparatus according to claim 7, wherein the chassis is connected to the control apparatus by a connector in such a manner as to be capable of being attached to and removed from the control apparatus; an in-chassis optical system code indicating information inherent to the collimator optical system and the pupil-projection optical system is provided on the chassis; an in-chassis-optical-system information reading apparatus for reading the in-chassis-optical-system code is provided in the connector; and the control apparatus controls the actuator based on the in-chassis-optical-system code that is read.

12. An optical-scanning microscope examination apparatus comprising:
a light source that emits light;
a light-transmitting member configured to transmit the light emitted by the light source;
a collimator optical system for converting the light transmitted by the light-transmitting member to a collimated beam;
a beam-scanning unit for scanning the collimated beam issuing from the collimator optical system on a subject;
a focusing optical system for focusing the beam scanned by the beam-scanning unit on the subject;
a pupil-projection optical system disposed between the focusing optical system and the beam-scanning unit;
a light detector for detecting return light returning from the subject via the focusing optical system, the pupil-projection optical system, the beam-scanning unit, the collimator optical system, and the light-transmitting member;
an actuator for moving the end portion of the light-transmitting member, the collimator optical system, or the pupil-projection optical system in the optical-axis direction; and
a control apparatus for controlling driving of the actuator,
wherein an end portion of the light-transmitting member, the collimator optical system, the beam-scanning unit, and the pupil-projection optical system are accommodated inside a chassis,
the focusing optical system is attached to the chassis in such a manner as to be capable of being attached and removed, and
a code indicating information inherent to the focusing optical system is provided in the focusing optical system; a reading apparatus for reading the code is provided in the chassis; and
the control apparatus controls the actuator based on the code that is read.

13. An optical-scanning microscope examination apparatus according to claim 12 further comprising a database for associating and storing the code and the information inherent to the focusing optical system, wherein the control apparatus searches the database using as a key the code read by the reading apparatus and controls the actuator based on the obtained information inherent to the focusing optical system.

14. An optical-scanning microscope examination apparatus according to claim 12, wherein the chassis is connected to the control apparatus via a connector in such a manner as to be capable of being attached to and removed from the control apparatus; an in-chassis-optical-system code indicating information inherent to the collimator optical system and the pupil-projection optical system is provided in the chassis; an in-chassis-optical-system information reading apparatus for reading the in-chassis-optical-system code is provided in the connector; and the control apparatus controls the actuator based on the in-chassis-optical-system code that is read.

15. An optical-scanning microscope examination apparatus according to claim 14, further comprising a second database for associating and storing the in-chassis-optical-system code and information inherent to the collimator optical system and the pupil-projection optical system, wherein the control apparatus searches the second database using as a key the in-chassis-optical-system code read by the in-chassis-optical-system information reading apparatus and controls the actuator based on the obtained information.

16. An optical-scanning microscope examination apparatus according to claim 12, further comprising an image-information inputting unit for inputting image information of the image to be acquired by the light detector, wherein the control apparatus controls the actuator based on the image information.

17. An optical-scanning microscope examination apparatus according to claim 16, wherein the image-information inputting unit is provided on an outer face of the chassis.

18. An optical-scanning microscope examination apparatus according to claim 12, further comprising a position detector for detecting the position of the end portion of the light-transmitting member, the collimator optical system, or the pupil-projection optical system, which are moved by the actuator.

19. An optical-scanning microscope examination apparatus according to claim 18, further comprising an image-information calculating unit for calculating the image information of the image to be acquired by the light detector based on the position of the end portion of the light-transmitting member, the collimator optical system, or the pupil-projection optical system detected by the position detecting unit, and an image-information display unit for displaying the calculated image information.

20. An optical-scanning microscope examination apparatus according to claim 18, further comprising:
an inherent-information inputting unit for inputting inherent information of the focusing optical system;
an image-information calculating unit for calculating the image information for the image to be acquired by the light detector based on the position of the end portion of the light-transmitting member, the collimator optical system, or the pupil-projection optical system detected by the prostitution detecting unit and the input information inherent to the focusing optical system; and
an image-information display unit for displaying the calculated image information.

21. An optical-scanning microscope examination apparatus according to claim 18, further comprising:
an optical-system-information inputting unit for inputting information inherent to the collimator optical system and the pupil-projection optical system;
an image-information calculating unit for calculating the image information of the image to be acquired by the light detector based on the position of the end portion of the light-transmitting member, the collimator optical system, or the pupil-projection optical system detected by the position detecting unit and the input information inherent to the collimator optical system and the pupil-projection optical system; and
an image-information display unit for displaying the calculated image information.

22. A storage container for accommodating a focusing optical system of a laser-scanning microscope that includes
a beam-scanning unit including an optical fiber, a collimator mechanism, and a beam-scanning mechanism;
a focusing optical system which has a long, thin, rigid, cylindrical inserting portion and which is attached to the beam-scanning unit in such a manner as to be capable of being attached and removed,
wherein the storage container comprises:
a code for indicating information inherent to the focusing optical system.

23. A storage container according to claim 22 further comprising a guard mechanism that is capable of accommodating only the focusing optical system corresponding to the code.

24. An optical-scanning microscope examination apparatus comprising:
a light source that emits light;
an optical fiber configured to transmit light emitted by the light source;
an apparatus main body accommodating a collimator optical system which converts the light transmitted by the optical fiber into a collimated beam, and a beam-scanning mechanism for two-dimensionally scanning the collimated beam emitted from the collimator optical system;
an objective unit which is attached to the apparatus main body in such a manner as to be capable of being attached and removed and which focuses the beam scanned by the beam-scanning mechanism at an examination site of a subject; and
a light detector for detecting return light returning via the objective unit, the apparatus main body, and the optical fiber,
wherein the objective unit has an end portion that is capable of being inserted inside the subject,
a mechanism for attaching and detaching the objective unit to the main body includes a rotation stop for stopping relative rotation of the objective unit, about a longitudinal axis, with respect to the apparatus main body during attachment and detachment,
a pupil-projection optical system for forming an intermediate image of the beam scanned by the beam-scanning mechanism is provided in the apparatus main body,
abutting surfaces that abut when the apparatus main body and the objective unit are coupled together are provided, and
the position of the abutting surfaces in the optical-axis direction is disposed at a position substantially coincident with the position of the intermediate image in the optical-axis direction.

25. An optical-scanning microscope examination apparatus according to claim 24, wherein the mechanism for attaching and detaching includes a first screw which is held on one of the apparatus main body and the objective unit in such a manner as to be freely rotatable about the longitudinal axis, and a second screw which is provided on the other one of the apparatus main body and the objective unit and which is fastened to the first screw.

26. An optical-scanning microscope examination apparatus according to claim 24, wherein marks which are aligned when the objective unit is attached to the apparatus main body are provided on the apparatus main body and the objective unit.

27. An optical-scanning microscope examination apparatus according to claim 24, wherein an insertion-depth detecting unit for detecting the insertion depth of the objective lens unit is provided on the outer circumference of the objective unit.

28. An optical-scanning microscope examination apparatus according to claim 24, wherein anti-reflection treatment is applied to the outer circumference of the objective unit.

* * * * *